United States Patent [19]

Katano et al.

[11] Patent Number: 5,399,566
[45] Date of Patent: Mar. 21, 1995

[54] PYRIDINE DERIVATIVES HAVING ANGIOTENSIN II ANTAGONISM

[75] Inventors: Kiyoaki Katano; Hiroko Ogino; Eiki Shitara; Hiromi Watanabe; Jun Nagura; Naomi Osada; Yasuyuki Ichimaru; Fukio Konno; Tomoya Machinami; Takashi Tsuruoka, all of Yokohama, Japan

[73] Assignee: Meiji Seika Kabushiki Kaisha, Tokyo, Japan

[21] Appl. No.: 752,557

[22] PCT Filed: Jun. 19, 1991

[86] PCT No.: PCT/JP91/00822
§ 371 Date: Sep. 10, 1991
§ 102(e) Date: Sep. 10, 1991

[87] PCT Pub. No.: WO91/19697
PCT Pub. Date: Dec. 26, 1991
(Under 37 CFR 1.47)

[30] Foreign Application Priority Data

Jun. 19, 1990 [JP] Japan .................................. 2-158585
Sep. 19, 1990 [JP] Japan .................................. 2-247178
Jan. 22, 1991 [JP] Japan .................................. 3-081067

[51] Int. Cl.$^6$ .................... C07D 401/10; A61K 31/44
[52] U.S. Cl. .................................. 514/340; 514/345; 514/348; 514/349; 514/350; 514/351; 546/275; 546/290; 546/296; 546/297; 546/300; 546/301; 546/302; 546/304
[58] Field of Search ............... 546/276, 290, 296, 297; 514/340, 345, 349, 348, 350, 351

[56] References Cited

U.S. PATENT DOCUMENTS 5,250,548 10/1993 Winn et al. ..................... 514/340

FOREIGN PATENT DOCUMENTS

| 0323841 | 7/1989 | European Pat. Off. . |
| 0392317 | 10/1990 | European Pat. Off. . |
| 0399731 | 11/1990 | European Pat. Off. . |
| 0401030 | 12/1990 | European Pat. Off. . |
| 0407342 | 1/1991 | European Pat. Off. . |
| 0411766 | 2/1991 | European Pat. Off. . |
| 0419048 | 3/1991 | European Pat. Off. . |
| 0424317 | 4/1991 | European Pat. Off. . |
| 445811 | 9/1991 | European Pat. Off. . |
| 0453210 | 10/1991 | European Pat. Off. . |
| 0475206 | 3/1992 | European Pat. Off. . |

OTHER PUBLICATIONS

Carini et al., "Nonpeptide Angiotensin II Receptor Antagonists: N-[(Benzyloxy)benzyl]imidazoles and Related Compounds as Potent Antihypertensives", J. Med. Chem. 1990, 33, 1330–1336.

Primary Examiner—Jane T. Fan
Attorney, Agent, or Firm—Wenderoth, Lind & Ponack

[57] ABSTRACT

The invention provides compounds represented by the following formula (I)

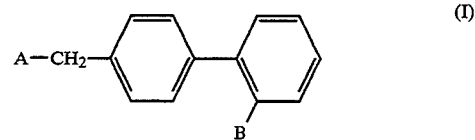

or a pharmaceutically acceptable salts thereof wherein A represents

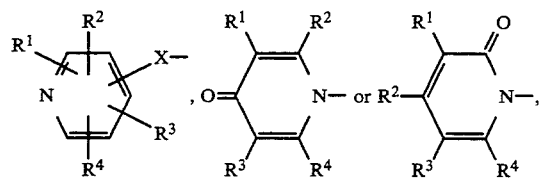

B represents a carboxy or tetrazolyl group; and
X represents —O—, —NH— or —S(O)$_r$—.

The compounds possess angiotensin II antagonism, and may be used as an antihypertensive agent, a therapeutic agent to congestive heart failure, an antianxiety agent and a cognitive enhancing agent.

11 Claims, No Drawings

PYRIDINE DERIVATIVES HAVING ANGIOTENSIN II ANTAGONISM

BACKGROUND OF THE INVENTION

1. Field of the Invention

This invention relates to pyridine derivatives having angiotensin II antagonism, processes for their preparation and a pharmaceutical composition containing at least one of them as an antihypertensive agent usable in the treatment of hypertension, as a therapeutic agent for the treatment of congestive heart failure, as an antianxiety agent, and as a cognitive enhancing agent.

2. Description of the Related Art

Angiotensin II is a hormone converted from angiotensin I by angiotensin converting enzyme, found in mammals including rat, dog and human as a strong pressor substance, and is one of the causes inducing hypertension. An inhibitor of angiotensin converting enzyme and an antagonist at angiotensin II receptor are now expected to be used in the treatment of hypertension and congestive heart failure. In addition, anxiolytic activity and cognitive enhancing activity based on the antagonism at angiotensin II receptor in brain have been reported in Neuro Report vol. 1, 15, (1990). They are, thus, expected to be used as an antianxiety agent and a cognitive enhancing agent. Captopril and Enalapril as inhibitors of angiotensin converting enzyme have been used clinically. While no antagonist at angiotensin II receptor is now used clinically, some peptide antagonists at angiotensin II receptor which are analogous to angiotensin II have been disclosed in Journal of Medicinal Chemistry, vol. 32, 466-, 898- and 1366-, 1989. As non-peptide antagonists at angiotensin II receptor, Japanese Patent Laid-Open Publication No. 240683/87 and EP-415886 specifications disclose imidazopyridine derivatives; Japanese Patent Publication No. 64428/88, Japanese Patent Laid-Open Publication No. 23868/88, WO/90-00281, WO/91-00277, EP-403158 and EP-403159 specifications disclose substituted imidazole derivatives; Japanese Patent Laid-Open Publication No. 287071/89, EP-411507, EP-412594 and EP-408332 specifications disclose substituted pyrrole, pyrazole and triazole derivatives; EP-411766 specification discloses quinazoline derivatives; Japanese Patent Laid-Open Publication No. 44377/91 and EP-419048 specification disclose pyrimidone derivatives; Japanese Patent Laid-Open Publication Nos. 5464/91, 27362/91 and 63264/91 and U.S. Patent No. 4,880,804 specifications disclose benzimidazole derivatives; EP-400974, EP-401030 and EP-407102 specifications disclose imidazole derivatives condensed with 5 to 7 membered ring. Pyridine derivatives as antagonists of angiotensin II receptor, however, have not been disclosed.

SUMMARY OF THE INVENTION

The inventors of the present invention have recently found that some pyridine derivatives have strong angiotensin II antagonism, and that they reveal, in the animal model, antihypertensive activity, anticardiac insufficiency activity, antianxiety activity and cognitive enhancing activity. The pyridine derivatives do not have agonist activity which is characteristic of peptide antagonists, and are excellent in oral absorption and duration of the activity. Furthermore, the angiotensin II antagonism of the pyridine derivatives is superior to that of conventional non-peptide angiotensin II antagonists.

Accordingly, an object of the present invention is to provide a novel pyridine derivative having angiotensin II antagonism.

Another object of the present invention is to provide a pharmaceutical composition comprising a novel pyridine derivative having angiotensin II antagonism, and particularly useful as an antihypertensive agent, an agent for congestive heart failure, an antianxiety agent, and a cognitive enhancing agent.

A further object of the present invention is to provide methods of treating hypertension, congestive heart failure and anxiety, and cognitive enhancing.

Pyridine derivatives according to the present invention are compounds represented by the following formula (I)

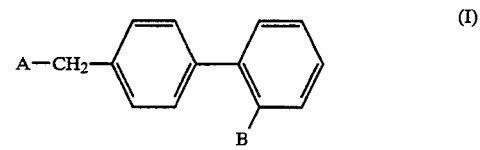

and pharmaceutically acceptable salts thereof wherein A represents

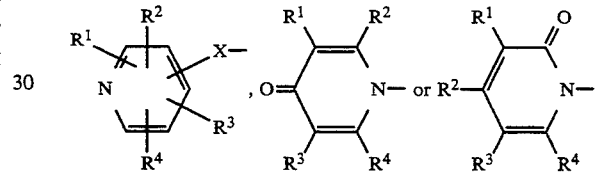

in which $R^1$, $R^2$, $R^3$ and $R^4$ each independently represents hydrogen; halogen; hydroxyl; nitro; cyano; phenyl; lower alkyl; lower haloalkyl; lower alkenyl; $C_{1-8}$ alkoxyl which may be optionally substituted by halogen, $C_{3-7}$ cycloalkyl, a five- or six-membered saturated heterocyclic ring which contains one nitrogen atom, may optionally contain one oxygen atom and may be optionally substituted by lower alkyl, or carbamoyl which may be optionally substituted by lower alkyl; lower alkenyloxy; $C_{3-7}$ cycloalkyloxy; benzyloxy which may be optionally substituted by halogen, lower alkyl, lower haloalkyl or lower alkoxyl; a group—$(CH_2)_mOR^5$ wherein m is an integer of 1 to 3, and $R^5$ is hydrogen, $C_{3-7}$ cycloalkyl, lower alkyl, lower alkenyl, benzyl, a group —$(CH_2)_nNR^6R^7$ in which n is an integer of 1 to 4, and $R^6$ and $R^7$ each independently represents hydrogen or lower alkyl, or may form a five- or six-membered saturated heterocyclic ring together with the nitrogen atom bonded thereto which ring may optionally contain one oxygen atom and may be optionally substituted by lower alkyl, or a group —$(CH_2)_pCOR^8$ in which p is an integer of 0 to 4, and $R^8$ is hydroxyl, lower alkyl, lower alkoxyl, phenyl or a group $NR^9R^{10}$ in which $R^9$ and $R^{10}$ each independently represents hydrogen or lower alkyl; a group —CO—$R^{11}$ wherein $R^{11}$ is hydrogen or lower alkyl; a group—$CONR^{12}R^{13}$ wherein $R^{12}$ and $R^{13}$ each independently represents hydrogen, lower alkyl or phenyl, or may form together with the nitrogen atom bonded thereto a five- or six-membered saturated heterocyclic ring which may optionally contain one oxygen atom; a group —COO—$R^{14}$ wherein $R^{14}$ represents hydrogen, lower alkyl, or a group —$(CH_2)_q$—$R^{15}$ in which q is an integer of 1 to 4, and $R^{15}$ is a five- or six-membered saturated heterocyclic ring which contains one or two nitrogen atoms, may optionally contain one oxygen atom and may be substituted by lower alkyl or phenyl-lower alkyl; or a group —$NR^{16}R^{17}$ wherein $R^{16}$ and $R^{17}$ each independently represents hydrogen, lower alkyl or lower acyl; or any two of $R^1$, $R^2$, $R^3$ and $R^4$ may form a group —$(CH_2)_r$— in which r is an integer of 3 or 4.

B represents a group $COOR^{18}$ wherein $R^{18}$ is hydrogen, lower alkyl or a group —$CH_2OCOC(CH_3)_3$, or tetrazolyl.

X represents —O—, —$NR^{19}$ in which $R^{19}$ is hydrogen, lower alkyl or lower acyl, or —$S(O)_t$— in which t is an integer of 0 to 2.

A pharmaceutical composition according to the present invention comprises at least one compound of formula (I) as defined above or a pharmaceutically acceptable salt thereof, together with at least one pharmaceutically acceptable carrier.

A method of treating hypertension, congestive heart failure and anxiety, and cognitive enhancing according to the present invention comprises administering to a mammal an effective amount of at least one compound of formula (I) as defined above or a pharmaceutically acceptable salt thereof.

DETAILED DESCRIPTION OF THE INVENTION

Compounds

In this Specification, the term "lower alkyl" or "lower alkoxyl" as a group or part of a group means that the group is a straight or branched alkyl group having 1 to 6, preferably 1 to 4, carbon atoms. The term "lower alkenyl" as a group or part of a group means that the group is a straight or branched group having 2 to 6, preferably 2 to 4, carbon atoms and contains at least one carbon-carbon double bond. The term "a halogen atom" includes a fluorine atom, a chlorine atom, a bromine atom, and an iodine atom. The term "haloalkyl" as a group or part of a group means an alkyl group in which one or more hydrogen atom(s) have been substituted by halogen atoms.

Preferred examples of the haloalkyl group represented by $R^1$, $R^2$, $R^3$ and $R^4$ include 2-fluoroethyl, difluoromethyl, trifluoromethyl and 2,2,2-trifluoroethyl.

The $C_{1-8}$ alkoxyl group represented by $R^1$, $R^2$, $R^3$ and $R^4$ is preferably $C_{1-6}$ alkoxyl group and may be optionally substituted by a halogen atom, a $C_{3-7}$ cycloalkyl group such as cyclopropyl, cyclobutyl, cyclopentyl, cyclohexyl or cycloheptyl, a five- or six-membered saturated heterocyclic ring which contains one nitrogen atom, may optionally contain one oxygen atom and may be optionally substituted by lower alkyl such as 1-pyrrolidinyl, 1-piperidinyl, 2,2,6,6-tetramethylpiperidin-1-yl, 4-methylpiperazin-1-yl, 4-diphenylmethylpiperazin-1-yl or morpholin-1-yl, or a carbamoyl group which may be optionally substituted by lower alkyl. In the case where the alkoxyl group is substituted by $C_{3-7}$ cycloalkyl, the five- or six-membered saturated heterocyclic ring containing one nitrogen atom, or the carbamoyl group, the number of carbons contained in the alkyl moiety of the alkoxyl group is preferably 1 to 3, and more preferably 1 or 2.

Preferred examples of the lower alkenyloxy group represented by $R^1$, $R^2$, $R^3$ and $R^4$ include vinyloxy, allyloxy, butenyloxy and cyclohexenyloxy.

The benzyl group represented by $R^1$, $R^2$, $R^3$, $R^4$ or may have substituents, and preferred examples of the benzyl group include o-, m- and p-methoxybenzyloxy, o-, m- and p-nitrobenzyloxy, o-, m- and p-methylbenzyloxy, o-, m- and p-chlorobenzyloxy, o-, m- and p-fluorobenzyloxy, o-, m- and p-trifluoromethylbenzyloxy, o-, m- and p-hydroxybenzyloxy, o-, m- and p-aminobenzyloxy, and o-, m- and p-acetylaminobenzyloxy.

In the case where $R^5$ in the group —$(CH_2)_mOR^5$ represents $C_{3-7}$ cycloalkyl or lower alkyl, it is preferable that m be an integer of 1. Preferred examples of such a group includes (cyclopropyl)methyloxy, (cyclobutyl)-$_m$ethyloxy, and (cyclopentyl)methyloxy.

In the group —$(CH_2)_nNR^6R^7$, n is preferably in the range of 1 to 3, and more preferably 1 or 2. The group $NR^6R^7$ is preferably amino, methylamino, dimethylamino, ethylamino, diethylamino, isopropylamino or diisopropylamino. $R^6$ and $R^7$ may form, together with the nitrogen atom bonded thereto, a five- or six-membered saturated heterocyclic ring which may optionally contain one oxygen atom. Preferred examples of such a heterocyclic ring are the same as the above.

In the group $(CH_2)_pCOR^8$, p is preferably an integer of from 0 to 2, and more preferably 0 or 1.

In the group —$CONR^{12}R^{13}$, $R^{12}$ and $R^{13}$ may form, together with the nitrogen atom bonded thereto, a five- or six-membered saturated heterocyclic ring which may optionally contain one oxygen atom. Preferred examples of the heterocyclic ring are the same as the above.

In the group —$(CH_2)_q$—$R^{15}$ represented by $R^{14}$, q is preferably an integer of from 1 to 3, more preferably 2. Preferred examples of a five- or six-membered saturated heterocyclic ring, represented by $R^{15}$, containing one or two nitrogen atoms and optionally one oxygen atom include pyrrolidinyl, piperidinyl, pyrazolidinyl, piperazinyl and morpholinyl.

A preferred class of compounds of formula (I) is that wherein A represents a group of formula

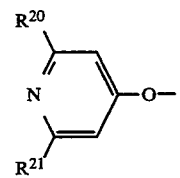

in which $R^{20}$ and $R^{21}$ each independently represents lower alkyl, phenyl, or a group —$(CH_2)_mOR^5$ is as defined in formula (I).

Another preferred class of compounds of formula (I) is that wherein A represents a group of formula

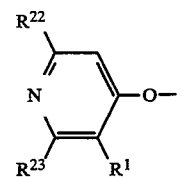

in which $R^{22}$ and $R^{23}$ each independently represents methyl or ethyl, and $R^1$ is as defined in formula (I).

A further preferred class of compounds of formula (I) is that wherein A represents a group of formula

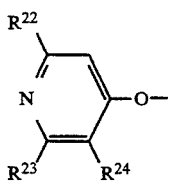

in which $R^{22}$ and $R^{23}$ are as defined above, and $R^{24}$ represents a $C_{1-8}$ alkoxyl group which may be optionally substituted by halogen, $C_{3-7}$ cycloalkyl, a five- or six-membered saturated heterocyclic ring which contains one nitrogen atom, may optionally contain one oxygen atom and may be optionally substituted by lower alkyl, or carbamoyl which may be optionally substituted by lower alkyl.

Yet another preferred class of compounds of formula (I) is that wherein A represents a group of formula

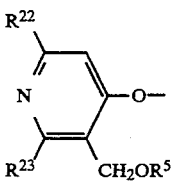

in which $R^{22}$ and $R^{23}$ are as defined above, and $R^5$ is as defined in formula (I).

Another preferred class of compounds of formula (I) is that wherein A represents a group of formula

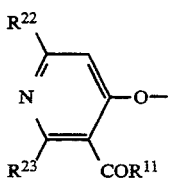

in which $R^{22}$ and $R^{23}$ are as defined above, and $R^{11}$ is as defined in formula (I).

Another preferred class of compounds of formula (I) is that wherein A represents a group of formula

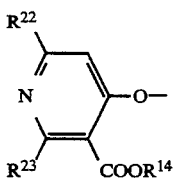

in which $R^{22}$ and $R^{23}$ are as defined above, and $R^{14}$ is as defined in formula (I).

A further another preferred class of compounds of formula (I) is that wherein A represents a group of formula

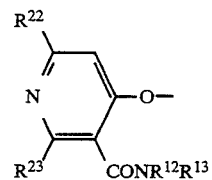

in which $R^{22}$ and $R^{23}$ are as defined above, and $R^{12}$ and $R^{13}$ are as defined in formula (I).

Another preferred class of compounds of formula (I) is that wherein A represents a group of formula

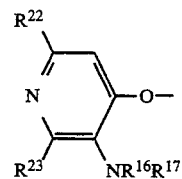

in which $R^{22}$ and $R^{23}$ are as defined above, and $R^{16}$ and $R^{17}$ are as defined in formula (I).

Particularly preferred compounds are:

2-ethyl-6-methyl-4-[2'-(tetrazol-5-yl)biphenyl-4-yl]-methoxypyridine;

2,6-diethyl-4-[2'-(tetrazol-5-yl)biphenyl-4-yl]-methoxypyridine;

2,6-diethyl-4-(2'-carboxybiphenyl-4-yl)$_m$ethoxypyridine;

2-ethyl-3-methoxy-6-methyl-4-[2'-(tetrazol-5-yl)biphenyl-4-yl]methoxypyridine;

3-methoxy-2,6-dimethyl-4-[2'-(tetrazol-5-yl)biphenyl-4-yl]methoxypyridine;

3-ethoxy-2,6-dimethyl-4-[2'-(tetrazol-5-yl)biphenyl-4-yl]methoxypyridine;

2,6-dimethyl-3-iso-propoxy-4-[2'-(tetrazol-5-yl)biphenyl-4-yl]methoxypyridine;

3-allyloxy-2,6-dimethyl-4-[2'-(tetrazol-5-yl)biphenyl-4-yl]methoxypyridine;

3-benzyloxy-2,6-dimethyl-4-[2'-(tetrazol-5-yl)biphenyl-4yl]-methoxypyridine;

3-ethoxy-2,6-dimethyl-4-(2'-carboxybiphenyl-4yl)methoxypyridine;

3-ethoxymethyl-2,6-dimethyl-4-[2'-(tetrazol-5-yl)-biphenyl-4-yl]methoxypyridine;

3-allyloxymethyl-2,6-dimethyl-4-[2'-(tetrazol-5-yl)-biphenyl-4-yl]methoxypyridine;

3-(cyclopropyl)methyloxymethyl-2,6-dimethyl-4-[2'-(tetrazol-5-yl)biphenyl-4-yl]methoxypyridine;

2,6-dimethyl-3-(N,N-dimethylcarbamoyloxy)methyl-4-[2'-(tetrazol-5-yl)biphenyl-4-yl]methoxypyridine;

3-acetyl-2,6-dimethyl-4-[2'-(tetrazol-5-yl)-biphenyl-4-yl]methoxypyridine;

3-formyl-2,6-dimethyl-4-[2'-(tetrazol-5-yl)biphenyl-4-yl]methoxypyridine;

3-ethoxycarbonyl-2,6-dimethyl-4-[2'-(tetrazol-5-yl)-biphenyl-4-yl]methoxypyridine;

3-ethoxycarbonyl-2,6-dimethyl-4-(2'-carboxybiphenyl-4-yl)methoxypyridine;

3-ethoxycarbonyl-2-ethyl-6-methyl-4-[2'-(tetrazol-5-yl)-biphenyl-4-yl]methoxypyridine;

3-ethoxycarbonyl-6-ethyl-2-methyl-4-[2'-(tetrazol-5-yl)-biphenyl-4-yl]methoxypyridine;

2-ethyl-3-methoxycarbonyl-6-methyl-4-[2'-(tetrazol-5-yl)-biphenyl-4-yl]methoxypyridine;

2,6-dimethyl-3-iso-propoxycarbonyl-4-[2'-(tetrazol-5-yl)-biphenyl-4-yl]methoxypyridine;

2,6-dimethyl-3-(N,N-dimethyl)carbamoyl-4-[2'-(tetrazol-5-yl)biphenyl-4-yl]methoxypyridine;

2,6-dimethyl-3-(piperidin-1-yl)carbonyl-4-[2-(tetrazol-5-yl)biphenyl-4-yl]methoxypyridine; a pharmaceutically acceptable salts thereof.

The compounds of the present invention give both stereoisomers and tautomers originated from the sulfur atom and the tetrazole ring contained therein, respectively. These isomers are also included in the present invention.

The compounds (I) of the present invention may form their salts. Preferred examples of such salts are non-toxic and pharmaceutically acceptable salts including alkaline metal and alkaline earth metal salts such as a sodium salt, a potassium salt and a calcium salt, salts of inorganic acid such as hydrogen fluoride, hydrogen chloride, hydrogen bromide and hydrogen iodide, nitric acid, perchloric acid, sulfuric acid and phosphoric acid, lower alkyl sulfonates such as methanesulfonate, trifluoromethanesulfonate and ethanesulfonate, aryl sulfonates such as benzenesulfonate and p-toluenesulfonate, organic acid salts such as fumarate, succinate, citrate, tartarate, oxalate and maleate, and amino acid salts such as glutamate and aspartate.

Preparation of Compounds

The compounds of the present invention can be prepared in one of the following methods:

According to the first method (A) of the present invention, a compound of formula (I), provided that t is 0 when X represents a group —S(O)$_t$—, can be prepared by reacting a compound of formula (II):

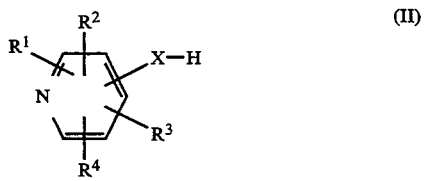

(II)

(wherein R$^1$, R$^2$, R$^3$ and R$^4$ are as defined in formula (I), and X is —O—, —NH— or —S—) with a compound of formula (III):

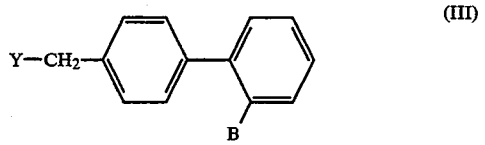

(III)

(wherein Y is a halogen atom or an alkyl or aryl sulfonyloxy group, and B is as defined in formula (I), provided that when B represents tetrazolyl, the tetrazolyl group may be protected) in a solvent which does not participate in the reaction, such as an organic solvent (e.g. N,N-dimethylformamide, dioxane, tetrahydrofuran, methanol, ethanol, acetone or dimethylsulfoxide), a mixed solvent of the organic solvents and water in the presence of a base at a temperature of from −30° C. to 150° C., preferably from 10° C. to 100° C., for 30 minutes to 24 hours, commonly for 1 to 6 hours, followed, if necessary, by removing any protecting groups.

Examples of Y in formula (III) include halogen atoms such as chlorine, bromine and iodine, alkylsulfonyloxy groups such as methanesulfonyloxy, ethanesulfonyloxy and trifluoromethanesulfonyloxy, and arylsulfonyloxy groups such as benzenesulfonyloxy and p-toluenesulfonyloxy. Examples of the base usable for the condensation reaction include alkaline metal hydroxides such as sodium hydroxide and potassium hydroxide, alkaline metal carbonates such as sodium hydrogencarbonate, potassium hydrogencarbonate, sodium carbonate and potassium carbonate, metal hydrides such as sodium hydride and potassium hydride, and organic amines such as triethylamine and pyridine.

Examples of protecting groups in the tetrazolyl group of B include trityl and 2-cyanoethyl.

According to the second method (B) of the present invention, a compound of formula (I), provided that t is 0 when X represents the group —S(O)$_t$—, can be obtained by reacting a compound of formula (IV):

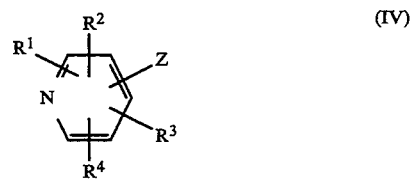

(IV)

(wherein R$^1$, R$^2$, R$^3$, and R$^4$ are as defined in formula (I), and Z represents halogen or nitro) with a compound of formula (V):

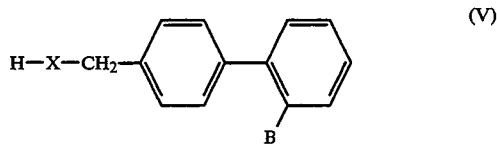

(V)

(wherein X is —O—, —NH— or —S—, and B is as defined in formula (I), provided that when B represents tetrazolyl, the tetrazolyl group may be protected), or with a reactive salt of the compound of formula (V) under the same conditions as in the method (A), followed, if necessary, by removing any protecting groups.

Examples of the reactive salt of the compound of formula (V) include alkaline metal salts such as a sodium salt, a potassium salt and a lithium salt.

According to the third method (C) of the present invention, a compound of formula (I), in which B represents tetrazolyl, can be prepared by converting other compound (I) in accordance with the following reaction scheme:

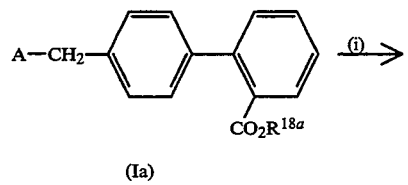

(Ia)

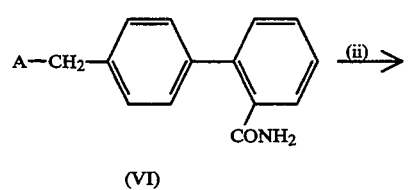

(VI)

-continued

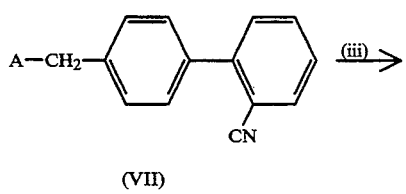

(VII)

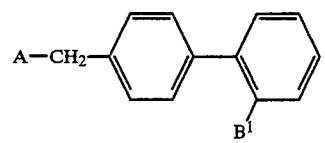

wherein A is as defined in formula (I), $R^{18a}$ is hydrogen or lower alkyl, preferably $C_{1-4}$ alkyl, and $B^1$ is tetrazolyl.

The step (i) is a process in which an amide having the formula (VI) is prepared by reacting a compound of formula (Ia) with ammonia. In the case where $R^{18a}$ in formula (Ia) is a hydrogen atom, it is preferable to convert the compound of formula (Ia) to an acid halide or an active ester before the reaction. Examples of the acid halide include acid chloride and acid bromide. Such an acid halide can be obtained by reacting the compound of formula (Ia) with an acid halide, such as thionyl chloride, thionyl bromide, phosphorus pentachloride, phosphorus oxychloride or oxalyl chloride, in the presence or absence of a solvent which does not participate in the reaction at temperature of from −20° C. to 150° C. Examples of the active ester include an ester of N-hydroxysuccinic imide and an ester of N-hydroxybenzotriazole.

The reaction between the compound of formula (Ia) and ammonia is conducted at a temperature of from 0° to 150° C. in a solvent such as water, methanol, ethanol, tetrahydrofuran or dioxane, and can be completed for 30 minutes to 24 hours.

The step (ii) is a process in which an amide of formula (VI) is converted to nitrile by dehydration reaction. The reaction is conducted with a dehydrating agent such as thionyl chloride, phosphorus pentachloride, phosphorus oxychloride or thionyl bromide in the presence or absence of a solvent which does not participate in the reaction at temperature of from −20° C. to 150° C., and can be completed for 30 minutes to 24 hours.

The step (iii) is a process in which a tetrazole ring is formed by reacting the nitrile with an azide derivative. The compound of formula (VII) is reacted with an azide derivative such as sodium azide, potassium azide, trimethyltin azide or tributyltin azide in the presence or absence of a solvent which does not participate in the reaction at a temperature of from 0° C. to 200° C. for 30 minutes to one week to form a tetrazole ring. If necessary, the tetrazole compound is protected by trityl, p-methoxybenzyl, methoxymethyl or 2-cyanoethyl, and then subjected to purification, followed by removing the protecting group to obtain the compound of formula (I) in which B represents a tetrazolyl group.

Alternatively, the compound of formula (VII) can be prepared by reacting the compound of formula (II) with 2′-cyano-4-bromomethylbiphenyl. This reaction can be conducted under the same conditions as in the method (A).

According to the method (D) of the present invention, a compound of following formula (Ib), which is included in the compounds of formula (I),

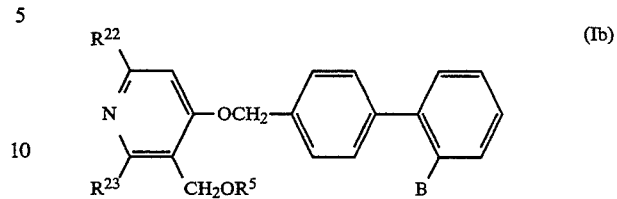

wherein $R^{22}$ and $R^{23}$ each independently represents methyl or ethyl, and $R^5$ and B are as defined in formula (I), can be prepared in accordance with the following reaction scheme:

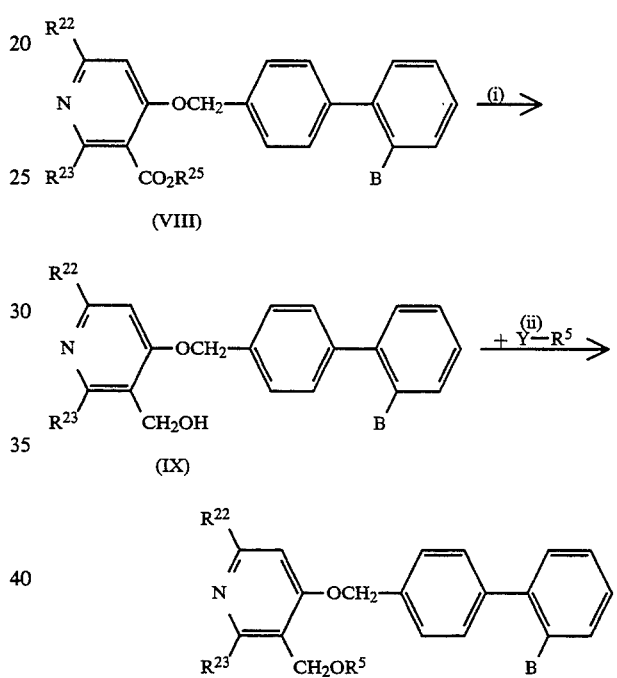

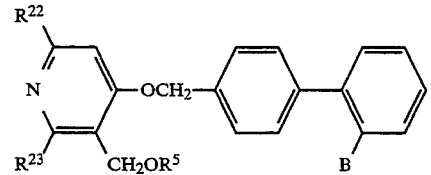

wherein $R^{22}$ and $R^{23}$ are as defined above, $R^5$ and B are as defined in formula (I), provided that when B represents tetrazolyl, the tetrazolyl group may be protected, $R^{25}$ represents lower alkyl, and Y is as defined in formula (III).

The step (i) is a process in which the compound of formula (VIII) is reduced to give the compound of formula (IX). A reducing agent usable in this process includes lithium aluminum hydride, sodium borohydride, and homologues thereof. A proper Lewis acid such as aluminum chloride or cesium chloride may be optionally co-employed in the reaction. The reaction is carried out in a solvent which does not participate in the reducing reaction, such as tetrahydrofuran, ether, dioxane, methanol, ethanol or dichloromethane, at a temperature of from 0° C. to 100° C. for 30 minutes to 48 hours.

The step (ii) is a process in which the compound of formula (IX) and a compound represented by Y—$R^5$ are subjected to condensation reaction, followed, if necessary, by removing any protecting groups to give the compound of formula (Ib). The reaction can be conducted under the same conditions as in the method (A).

According to the method (E) of the present invention, a compound of formula (Ic), which is included in the compounds of formula (I),

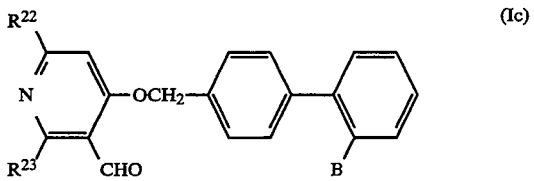

wherein $R^{22}$ and $R^{23}$ are as defined above, and B is as defined in formula (I), can be prepared by oxidizing the compound of formula (IX), followed, if necessary, by removing any protecting groups.

Oxidizing agents usable in this reaction process include manganese dioxide, nickel peroxide, chromic acid, a chromic acid-pyridine complex, dimethyl sulfoxide, and additives such as dicyclohexylcarbodiimide, acetic anhydride, trifluoroacetic anhydride and oxalyl chloride. The reaction is conducted in a solvent which does not participate in the oxidation, such as dichloromethane, dioxane, acetone, ethylether, pyridine or water, at a temperature of from −70° C. to 100° C. for 30 minutes to 24 hours.

According to the method (F) of the present invention, a compound of formula (Id), which is included in the compounds of formula (I),

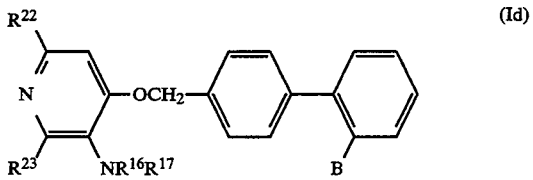

wherein $R^{22}$ and $R^{23}$ are as defined above, and $R^{16}$, $R^{17}$ and B are as defined in formula (I), can be prepared in accordance with the following reaction scheme:

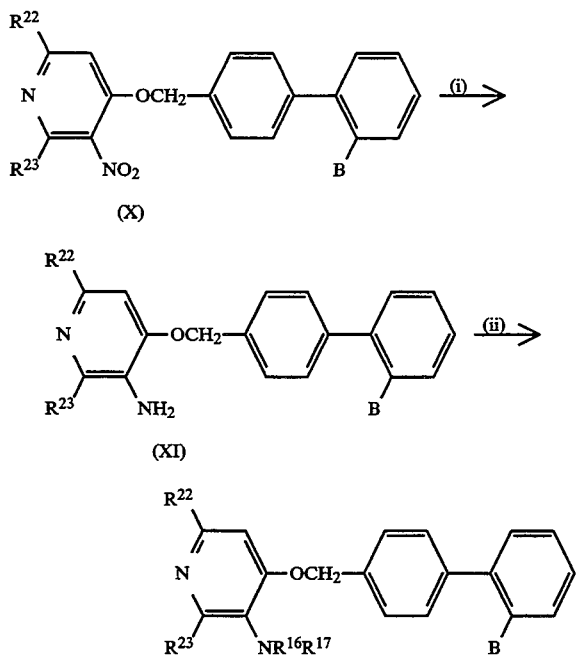

wherein $R^{22}$ and $R^{23}$ are as defined above, and $R^{16}$, $R^{17}$ and B are as defined in formula (I), provided that when B represents tetrazolyl, the tetrazolyl group may be protected.

The step (i) is a process in which the nitro group in the compound of formula (X) is reduced to give an amino compound. Reducing agents usable in this process include metals (e.g. iron, zinc and tin) and acids (e.g. acetic acid and hydrochloric acid); catalytic reduction (using a catalyst such as palladium, platinum or Raney nickel); and sodium borohydride. Water, methanol, ethanol and dioxane can be used as a solvent. The reaction is conducted in such a solvent which does not participate in the reaction, at a temperature of from 0° C. to 150° C. for 30 minutes to 24 hours.

The step (ii) is a process in which the compound of formula (XI) is alkylated or acylated, followed, if necessary, by removing any protecting groups to give the compound of formula (I).

The alkylating reaction is conducted in a solvent which does not participate in the reaction in the presence or absence of a base at a temperature of from −20° C. to 100° C. for 30 minutes to 24 hours. Alkylating agents usable in the reaction include alkyl halides such as methyl iodide, ethyl iodide, ethyl bromide, propyl iodide and butyl iodide, and alkylsulfonates such as methylmethanesulfonate, and methyl p-toluenesulfonate. In addition, alkylation using a metal hydride such as sodium borohydride or sodium cyanoborohydride with an aldehyde such as formaldehyde, acetaldehyde, propionaldehyde or butylaldehyde is also employable. Examples of the base for use in the reaction include alkaline metal hydroxides such as sodium hydroxide and potassium hydroxide, alkaline metal carbonates such as sodium hydrogencarbonate, potassium hydrogencarbonate, sodium carbonate and potassium carbonate, metal hydrides such as sodium hydride and potassium hydride, and organic bases such as pyridine, triethylamine and diisopropylethylamine.

The acylating reaction is conducted in a solvent which does not participate in the reaction in the presence or absence of a base at a temperature of from −20° C. to 100° C. for 30 minutes to 24 hours. Examples of an acylating agent usable in the above reaction include acid chlorides such as acetyl chloride and propionyl chloride, and acid anhydrides such as acetic anhydride and propionic anhydride. Examples of the base for use in the reaction include alkaline metal hydroxides such as sodium hydroxide and potassium hydroxide, alkaline metal carbonates such as sodium hydrogencarbonate, potassium hydrogencarbonate, sodium carbonate and potassium carbonate, metal hydrides such as sodium hydride and potassium hydride, and organic bases such as pyridine, triethylamine and diisopropylethylamine.

A sulfoxide compound or sulfone compound of formula (I), in which X represents the group —S(O)$_t$— and t is an integer of 1 or 2, can be prepared by oxidizing a compound of formula (I) in which X is —S—. This reaction is carried out in a solvent such as benzene, chloroform, methylene chloride, methanol, ethanol, acetic acid, formic acid, water or a mixture thereof by using an oxidizing agent. In the reaction, from 1 to 2 equivalents, preferably from 1 to 1.2 equivalents, of the oxidizing agent is employed to obtain a compound in which t is an integer of 1, and from 2 to 3 equivalents, preferably from 2 to 2.5 equivalents of the oxidizing agent is employed to obtain a compound in which t is an integer of 2. The reaction can be completed at temperature of from −40° C. to 60° C., preferably from −20° C. to room temperature, for 5 minutes to 6 hours. The oxidizing agents for use in the reaction include peracetic acid, hydrogen peroxide, trifluoroperacetic acid, methachloroperbenzoic acid, sodium methaperiodate, N-bromosuccinimide, tert.-butylhydroperoxide and manganese dioxide.

The pyridine and pyridone derivatives represented by formulae (II) and (IV) can be synthesized in accordance with any one of the known methods as described in the following specifications and journals: Japanese Laid-Open Patent Applications No. 178890/85, No. 17589/86, No. 148122/86 and No. 211581/89, Journal of Organic chemistry 26, 1673 (1961), ibid. 28, 725 (1963), ibid. 44, 870 (1979), ibid. 51, 268 (1986), Chemisches Berichte 54, 1089 (1921), ibid. 94, 486 (1961), Journal of Indian Chemical Society 101, 950 (1974), Journal of American Chemical Society 83, 193 (1961), Yakugaku Zasshi 91, 740 (1971), Bulletin of the Chemical Society of Japan 42, 2389 (1969), Heterocycles 13, 239 (1979), and Liebigs Ann. Chem. 1466 (1982).

The biphenyl derivatives represented by formulae (III) and (V) can be synthesized in accordance with any one of the known methods as described in the following specifications and journal: WO-89/06233, Japanese Laid-Open Patent Application No. 117876/89, and Journal of Organic Chemistry 56, 2395 (1991).

The compounds of formula (I) synthesized in the above methods can be purified by a usual manner such as recrystallization, reprecipitation, solvent extraction, silica gel column chromatography or column chromatography employing an adsorptive resin.

Use of compounds/pharmaceutical composition

The compound according to the present invention represented by formula (I) possesses angiotensin II antagonism. (Refer to experimental examples described below on the details of angiotensin II antagonism.) Thus, the compound according to the present invention is useful for the treatment and prophylaxis of the disorders in which angiotensin II is involved. In particular, the compound according to the present invention can be used as an antihypertensive agent, a therapeutic agent to congestive heart failure, an antianxiety agent and a cognitive enhancing agent.

The pharmaceutical composition containing the compound according to the present invention as an effective ingredient can be administered to animals including man and the other animals by any of the dosage routes such as oral administration and parenteral administration (for example, intravenous injection, intramuscular injection, subcutaneous administration, rectal administration or endermism).

Accordingly, the pharmaceutical composition containing the compound according to the present invention as an effective ingredient may take appropriate dosage forms depending on the dosage routes. In particular, it may be formulated into a variety of preparations such as injections, for example intravenous injection or intramuscular injection, oral preparations, for example capsules, tablets, granules, powder, pills, particulates or troches, preparations for rectal administration, oily or aqueous suppositories. These preparations may be formulated in a conventional manner using one or more pharmaceutically acceptable excipients, fillers, binding agents, wetting agents, disintegrating agents, surface active agents, lubricants, dispersants, buffers, conservatives, dissolution aids, preservatives, flavors, analgesics or stabilizers. As the above pharmaceutically acceptable non-toxic additives, there are mentioned, for example lactose, fructose, glucose, starch, gelatin, magnesium carbonate, synthetic magnesium silicate, talc, magnesium stearate, methyl cellulose, carboxylmethylcellulose or a salt thereof, gum arabic, polyethylene glycol, syrup, vaseline, glycerol, ethanol, propylene glycol, citric acid, sodium chloride, sodium sulfite, sodium phosphate or the like.

The content of the compound according to the present invention in the pharmaceutical composition depends on its dosage forms and usually is an amount of 1–70% by weight per total weight of the composition, preferably 5–50% by weight.

While the dose is determined appropriately depending on individual cases in consideration of the nature and severity of the condition being treated and of the age and sex of the patient, the proposed daily dose for adults is generally in an amount of about 0.1–1000 mg, preferably 1–200 mg, which is administered at one time or in several portions daily for the treatment of hypertension or heart failure. Further, the proposed daily dose for adults is generally in the range of about 0.1 μg –100 mg, preferably 1 μg –10 mg, which is administered at one time or in several portions daily for antianxiety and cognitive enhancing.

This invention will now be explained more specifically with reference to the following examples, which are given for illustrating this invention and are not intended to be limiting thereof.

The chemical shifts expressed in δ units (ppm) shown in the examples were obtained from NMR spectra recorded on a 400-MHz spectrometer using TMS as an internal standard.

Example 1

2,6-Diethyl-4-[2'-(tetrazol-5-yl)biphenyl-4-yl]-methoxypyridine:

(a) 115 mg of 60% sodium hydride was suspended in 2.4 ml of dried N,N-dimethylformamide, followed by stirring at room temperature for 20 minutes. To this suspension were added 363 mg of 2,6-diethyl-4(1H)-pyridone and 2.4 ml of N,N-dimethylformamide, followed by stirring for a further one hour.

Subsequently, a solution of 1.537 g of 4'- bromomethyl-2-(triphenylmethyltetrazol-5-yl)biphenyl in 7 ml of dried N,N-dimethylformamide was added to the reaction mixture. After stirring at room temperature for five hours, the mixture was stirred at 60° C. for 3.5 hours. After the reaction was completed, the reaction mixture was cooled to room temperature, to which was added 40 ml of cold water. The mixture was then extracted three times with 80 ml of ethyl acetate. The extract was washed with a saturated aqueous solution of sodium hydrogencarbonate, water and a saline solution successively, and then dried over anhydrous magnesium sulfate. The solvent was removed under reduced pressure, and the residue was purified by a silica gel column chromatography, whereby 1.22 g of a white powder of 2,6-diethyl-4-[2'-(triphenylmethyltetrazol-5-yl)biphenyl-4yl]methoxy-pyridine was obtained from the eluate of chloroform and ethyl acetate (25:1~5:1) (yield: 81%).

$^1$H NMR (CDCl$_3$) δ: 1.29 (6H, t), 2.78 (4H, q), 4.95 (2H, s), 6.57 (2H, s), 6.91 (6H, m), 7.17 (4H, m), 7.22–7.34 (9H), 7.40 (1H, dd), 7.47 (1H, dt), 7.51 (1H, dt), 7.95 (1H, dd);

FDMS (m/z): 628 (M+1)+

(b) 1.0 g of the compound obtained in the step (a) was dissolved in 12 ml of a 2:1 mixture of methanol and methylene chloride. To the solution was added 0.64 ml of 4N HCl while cooling with ice, followed by stirring at 10°–15° C. for 2.5 hours. After the reaction was completed, the pH of the reaction mixture was adjusted to 13 with 5N NaOH. After adding 10 ml of water, the reaction mixture was washed twice with 40 ml of diethylethyl ether. After neutralization, the organic solvent was removed under reduced pressure. The pH of the resulting reaction mixture was adjusted to 3–4 with 1N HCl while cooling with ice, followed by stirring at the temperature for approximately 30 minutes. The precipitated crystalline product was collected by filtration, washed with water and n-hexane, and then dried, whereby 530 mg of a colorless crystalline powder of the title compound was obtained (yield: 86%).

$^1$H NMR (DMSO-d$_6$) δ: 1.20 (6H, t), 2.65 (4H, q), 5.16 (2H, s), 6.79 (2H, s), 7.13 (2H, d), 7.39 (2H, d), 7.56 (2H, m), 7.68 (2H, m);

FDMS (m/z): 386 (M+1)+

Examples 2 to 37

Compounds of Examples 2 to 37 shown in Table 1 were obtained in the same manner as described in Example 1, in which various pyridones were respectively reacted, instead of 2,6-diethyl-4(1H)-pyridone employed in Example 1, with 4′-bromomethyl-2-(triphenylmethyltetrazol-5-yl)biphenyl and the protecting groups of the resulting compounds were removed respectively.

TABLE 1

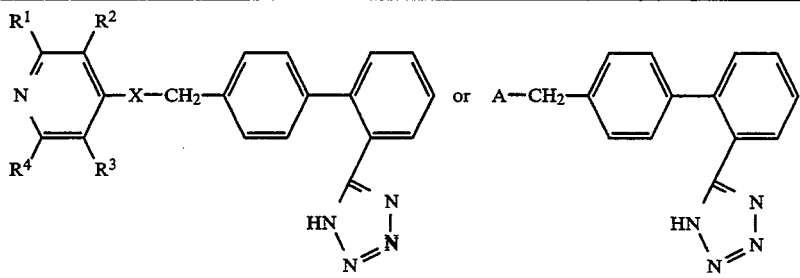

| Example | R$^1$ | R$^2$ | R$^3$ | R$^4$ | X | $^1$H NMR(DMSO-d$_6$) δ: MS(m/z): |
|---|---|---|---|---|---|---|
| 2 | CH$_3$ | H | H | CH$_3$ | O | 2.62(6H, s), 5.25(2H, s), 6.88(2H, s), 7.18(2H, d), 7.32(2H, d), 7.51(1H, d), 7.53(1H, dt), 7.62(1H, dt), 7.71(1H, d)*; FDMS(m/z): 358(M+1)+. *CDCl$_3$:CD$_3$OD = 10:1 |
| 3 | CH$_3$ | H | H | C$_2$H$_5$ | O | 1.19(3H, t), 2.40(3H, s), 2.66(2H, q), 5.15(2H, s), 6.80(2H, br. d), 7.13(2H, d), 7.38(2H, d), 7.57(2H, m), 7.67(1H, d), 7.67(1H, t); FDMS(m/z): 372(M+1)+. |
| 4 | CH$_3$ | H | H | n-C$_3$H$_7$ | O | 0.89(3H, t), 1.65(2H, sext), 2.39(3H, s), 2.60(2H, t), 5.15 (2H, s), 6.79(2H, d), 7.13(2H, d), 7.38(2H, d), 7.56(2H, m), 7.66(2H, m); FDMS(m/z): 386(M+1)+. |
| 5 | CH$_3$ | H | H | i-C$_3$H$_7$ | O | 1.28(6H, s), 2.58(3H, s), 3.21(1H, m), 5.19(2H, s), 6.78(2H, br. s), 7.14(2H, d), 7.28(2H, d), 7.45(1H, dd), 7.49(1H, dt), 7.57(1H, dt), 7.74(1H, dd)*; FDMS(m/z): 386(M+1)+. *CDCl$_3$:CD$_3$OD = 1:1 |
| 6 | CH$_3$ | H | H | n-C$_4$H$_9$ | O | 0.89(3H, t), 1.31(2H, m), 1.62(2H, m), 2.43(3H, s), 2.67(2H, t), 5.19(2H, s), 6.89(2H, d), 7.14(2H, d), 7.39(2H, d), 7.57 (2H, m), 7.67(2H, m); FDMS(m/z): 400(M+1)+. |
| 7 | CH$_3$ | H | H | Ph | O | 2.42(3H, s), 5.10(2H, s), 6.69(1H, d), 7.04(2H, d), 7.06(1H, d), 7.26(2H, d), 7.28~7.32(3H, m), 7.33(1H, d), 7.41(1H, dt), 7.51(1H, dt), 7.67~7.72(2H, m), 7.77(1H, d)*; FDMS(m/z): 420(M+1)+. *CDCl$_3$ |
| 8 | CF$_3$ | H | H | CF$_3$ | O | 5.41(2H, s), 7.17(2H, d), 7.44(2H, d), 7.57(1H, d), 7.59(1H, t), 7.68(1H, d), 7.69(1H, t), 7.91(2H, s); EIMS(m/z): 465(M+) |
| 9 | CH$_3$ | CH$_3$ | H | CH$_3$ | O | 2.09(3H, s), 2.42(3H, s), 2.43(3H, s), 5.22(2H, s), 7.03(1H, s), 7.15(2H, d), 7.39(2H, d), 7.55(2H, m), 7.66(2H, m); FDMS(m/z): 372(M+1)+. |
| 10 | CH$_3$ | CH$_3$ | CH$_3$ | CH$_3$ | O | 2.10(6H, s), 2.35(6H, s), 4.80(2H, s), 7.15(2H, d), 7.41(2H, d), 7.57(1H, d), 7.58(1H, t), 7.68(1H, d), 7.69(1H, t); EIMS (m/z): 385(M+). |
| 11 | CH$_3$ | OCH$_3$ | H | CH$_3$ | O | 2.37(3H, s), 2.41(3H, s), 3.72(3H, s), 5.24(2H, s), 7.11(1H, s), 7.16(2H, d), 7.42(2H, d), 7.59(2H, dd), 7.69(2H, d), 7.72 (1H, br. s); FDMS(m/z): 388(M+1)+. |
| 12 | CH$_3$ | OC$_2$H$_5$ | H | CH$_3$ | O | 1.23(3H, t), 2.32(3H, s), 2.35(3H, s), 3.93(2H, q), 5.18(2H, s), 6.95(1H, s), 7.14(2H, d), 7.39(2H, d), 7.58(2H, m), 7.67 (2H, m); FDMS(m/z): 401(M+1)+. |
| 13 | CH$_3$ | O(-i-C$_3$H$_7$) | H | CH$_3$ | O | 1.18(6H, d), 2.32(3H, s), 2.36(3H, s), 4.35(1H, m), 5.16(2H, s), 6.94(1H, s), 7.14(2H, d), 7.39(2H, d), 7.57(2H, t), 7.66 (2H, d); SIMS(m/z): 416(M+1)+. |
| 14 | CH$_3$ | O(-n-C$_4$H$_9$) | H | CH$_3$ | O | 0.86(3H, t), 1.39(2H, m), 1.63(2H, m), 2.37(3H, s), 2.41(3H, s), 4.01(2H), 5.21(2H, s), 7.08(1H, s), 7.15(2H, d), 7.40(2H, d), 7.53~7.67(4H, m); EIMS(m/z): 429(M+). |
| 15 | CH$_3$ | O(CH$_2$)$_4$CF$_3$ | H | CH$_3$ | O | 1.60~1.76(4H, m), 2.20~2.30(2H, m), 2.32(3H, s), 2.35(3H, s), 3.87(2H, t), 5.17(2H, s), 6.96(1H, s), 7.13(2H, d), 7.39(2H, d), 7.53~7.71(4H, m); EIMS(m/z): 497(M+). |
| 16 | C$_2$H$_5$ | OCH$_3$ | H | CH$_3$ | O | 1.23(3H, t), 2.51(3H, s), 2.86(2H, q), 3.83(3H, s), 5.42(2H, s), 7.19(2H, d), 7.47(2H, d), 7.58~7.73(5H, m)*; SIMS |

TABLE 1-continued

| Example | R¹ | R² | R³ | R⁴ | X | ¹H NMR(DMSO-d$_6$) δ: MS(m/z): |
|---|---|---|---|---|---|---|
| 17 | $CH_3$ | $OCH_2CH=CH_2$ | H | $CH_3$ | O | (m/z): 402(M+1)⁺. *CDCl$_3$ 2.31(3H, s), 2.34(3H, s), 4.42(2H, d), 5.14(2H, s), 5.18(1H, d), 5.30(1H, d), 6.01(1H, m), 6.94(1H, s), 7.14(2H, d), 7.30~7.60(6H, m); SIMS(m/z): 414(M+1)⁺. |
| 18 | $CH_3$ | $OCH_2$-cyclopropyl | H | $CH_3$ | O | 0.19(2H, m), 0.48(2H, m), 1.10(1H, m), 2.31(3H, s), 2.34(3H, s), 3.71(2H, d), 5.22(2H, s), 7.00(1H, s), 7.13(2H, m), 7.36~7.68(6H, m); SIMS(m/z): 428(M+1)⁺. |
| 19 | $CH_3$ | $O(CH_2)_2$-N(C(CH$_3$)$_2$-)$_2$ (2,2,6,6-tetramethylpiperidinyl) | H | $CH_3$ | O | 1.02(12H, s), 1.39~1.46(6H, m), 2.33(3H, s), 2.35(3H, s), 2.92(2H, t), 3.80(2H, t), 5.15(2H, s), 6.97(1H, s), 7.12(2H, d), 7.37(2H, d), 7.46~7.67(4H, m); SIMS(m/z): 541(M+1)⁺. |
| 20 | $CH_3$ | $OCH_2CON(i-C_3H_7)_2$ | H | $CH_3$ | O | 1.01(6H, d), 1.30(6H, d), 2.35(3H, s), 2.37(3H, s), 3.42(1H, m), 3.94(1H, m), 4.49(2H, s), 5.17(2H, s), 6.95(1H, s), 7.14(2H, d), 7.42(2H, d), 7.52(1H, dd), 7.57(1H, dt), 7.67(1H, dd) 7.68(1H, dt); SIMS(m/z): 515(M+1)⁺. |
| 21 | $CH_3$ | $OCH_2Ph$ | H | $CH_3$ | O | 2.42(3H, s), 2.62(3H, s), 5.02(2H, s), 5.44(2H, s), 7.19(2H, d), 7.36(5H), 7.48(2H, d), 7.59(3H, m), 7.70(2H, m); SIMS(m/z): 463(M+1)⁺. |
| 22 | $CH_3$ | $OCH_2$-(4-CH$_3$-C$_6$H$_4$) | H | $CH_3$ | O | 2.30(3H, s), 2.35(3H, s), 2.54(3H, s), 4.95(2H, s), 5.38(2H, s), 7.15~7.24(6H, m), 7.47~7.49(3H, m), 7.60~7.63(2H, m), 7.69~7.74(2H, m); SIMS(m/z): 478(M+1)⁺. |
| 23 | $CH_3$ | $OCH_2$-(3-CH$_3$-C$_6$H$_4$) | H | $CH_3$ | O | 2.26(3H, s), 2.26(3H, s), 2.35(3H, s), 4.85(2H, s), 5.20(2H, s), 6.97(1H, s), 7.11~7.67(12H, m); SIMS(m/z): 478(M+1)⁺. |
| 24 | $CH_3$ | $OCH_2$-(2-CH$_3$-C$_6$H$_4$) | H | $CH_3$ | O | 2.24(3H, s), 2.25(3H, s), 2.36(3H, s), 4.90(2H, s), 5.20(2H, s), 7.01(1H, s), 7.13~7.70(12H, m); SIMS(m/z): 478(M+1)⁺. |
| 25 | $CH_3$ | $OCH_2$-(4-Cl-C$_6$H$_4$) | H | $CH_3$ | O | 2.27(3H, s), 2.36(3H, s), 4.90(2H, s), 5.20(2H, s), 6.99(1H, s), 7.14(2H, d), 7.36~7.42(6H, m), 7.55~7.60(2H, m), 7.67~7.71(2H, m); SIMS(m/z): 498(M+1)⁺. |
| 26 | $CH_3$ | $OCH_2$-(4-F-C$_6$H$_4$) | H | $CH_3$ | O | 2.25(3H, s), 2.36(3H, s), 4.89(2H, s), 5.21(2H, s), 7.00(1H, s), 7.14~7.19(4H, m), 7.38~7.44(4H, m), 7.58(2H, t), 7.66~7.72(2H, m); SIMS(m/z): 482(M+1)⁺. |
| 27 | $CH_3$ | $OCH_2$-(4-CF$_3$-C$_6$H$_4$) | H | $CH_3$ | O | 2.29(3H, s), 2.37(3H, s), 5.00(2H, s), 5.20(2H, s), 7.00(1H, s), 7.13(2H, d), 7.41(2H, d), 7.54~7.61(4H, m), 7.67~7.73(4H, m); SIMS(m/z): 532(M+1)⁺. |

TABLE 1-continued

| Example | A R¹ | R² | R³ | R⁴ | X | ¹H NMR(DMSO-d₆) δ: MS(m/z): |
|---|---|---|---|---|---|---|
| 28 | CH₃ | COCH₃ | H | CH₃ | O | 2.38(3H, s), 2.47(3H, s), 2.50(3H, s), 5.14(2H, s), 6.68(1H, s), 7.16(2H, d), 7.28(2H, d), 7.48~7.55(3H, m), 7.76~7.83 (2H, m)*; EIMS(m/z): 399(M⁺). *CDCl₃:CD₃OD = 10:1 |
| 29 | CH₃ | CN | H | CH₃ | O | 2.55(3H, s), 2.66(3H, s), 5.13(2H, s), 6.74(1H, s), 7.19~7.33 (4H, m), 7.43~7.48(3H, m), 7.64~7.66(1H, m)*; IR(KBr)cm⁻¹: 2250. *CDCl₃:CD₃OD = 10:1 |
| 30 | CH₃ | NO₂ | H | CH₃ | O | 2.39(3H, s), 2.49(3H, s), 5.32(2H, s), 7.14(2H, d), 7.27(1H, s), 7.34(2H, d), 7.58(1H, d), 7.59(1H, t), 7.69(1H, d), 7.70 (1H, t); EIMS(m/z): 402(M⁺). |
| 31 | CH₃ | OCH₃ | H | CH₂OH | O | 2.42(3H, s), 3.76(3H, s), 4.54(2H, s), 5.30(2H, s), 7.16(2H, d), 7.31(1H, br. s), 7.45(2H, d), 7.59(2H, br. s), 7.67~7.73 (3H, m); FDMS(m/z): 404(M+1)⁺. |
| 32 | CH₂OCH₃ | OCH₃ | H | CH₂OCH₃ | O | 3.26(3H, s), 3.43(3H, s), 3.88(3H, s), 3.42(2H, s), 4.50(2H, s), 5.14(2H, s), 7.01(1H, s), 7.17(2H, d), 7.30(2H, d), 7.45 (1H, d), 7.54(1H, t), 7.60(1H, t), 8.03(1H, d)*; FDMS(m/z): 448(M+1)⁺. *CDCl₃ |
| 33 | CH₃ | H | H | CH₃ | NH | 2.35(6H, s), 4.45(2H, s), 6.63(2H, s), 7.12(2H, d), 7.17(2H, d), 7.36(1H, d), 7.40(1H, t), 7.45(1H, t), 7.53(1H, d)*; EIMS (m/z): 356(M⁺). *DMSO-d₆:CD₃OD = 5:1 |
| 34 | CH₃ | H | H | CH₃ | S | 2.36(6H, s), 4.32(2H, s), 6.99(2H, s), 7.06(2H, d), 7.36(2H, d), 7.56(2H, m), 7.66(2H, m); EIMS(m/z): 373(M⁺). |
| 35 | \multicolumn{5}{H₃C-pyridine-O— structure} | | 2.35(3H, s), 2.36(3H, s), 5.11(2H, s), 7.02(1H, d), 7.12(2H, d), 7.30(1H, d), 7.39(2H, d), 7.58(2H, t), 7.65~7.72(2H, m); EIMS(m/z): 357(M⁺). |
| 36 | \multicolumn{5}{H₃C-pyridine-O— structure} | | 2.40(3H, s), 5.13(2H, s), 7.12(2H, d), 7.18(1H, d), 7.37(1H, dd), 7.39(2H, d), 7.57(1H, d), 7.58(1H, t), 7.67(1H, d), 7.69 (1H, t), 8.22(1H, d); EIMS(m/z): 343(M⁺). |
| 37 | \multicolumn{5}{H₃CO-pyridone-N— structure} | | 3.71(3H, s), 5.11(2H, s), 6.18(1H, t), 6.81(1H, dd), 7.06(2H, d), 7.20(2H, d), 7.35(1H, dd), 7.55(2H, m), 7.66(2H, m); SIMS(m/z): 360(M+1)⁺. |

Example 38

2,6-Dimethyl-3-(p-methoxybenzyloxy)-4-[2'-(tetrazol-5-yl)biphenyl-4-yl]methoxypyridine:

(a) The procedure in Example 1 was repeated employing 2,6-dimethyl-3-(p-methoxybenzyloxy)-4-(1H)-pyridone, whereby a light-yellow powder of 2,6-dimethyl-3-(p-methoxybenzyloxy)-4-[2'-(triphenylmethyltetrazol-5-yl)biphenyl-4-yl]methoxypyridine was obtained (yield: approximately 100%).

¹H NMR (CDCl₃) δ: 2.37 (3H, s), 2.44 (3H, s), 3.78 (3H, s), 4.90 (2H, s), 5.04 (2H, s), 6.63 (1H, s), 6.83 (2H, d), 6.89–6.94 (6H), 7.16–7.32 (15H), 7.42 (1H, dd), 7.47 (1H, dt), 7.52 (1H, dt), 7.94 (1H, dd);

SIMS (m/z): 736 (M+1)⁺

(b) 200 mg of the compound obtained in the step (a) was dissolved in a mixture of 2 ml of dioxane and 2 ml of ethanol, to which was added 2 ml of concentrated aqueous ammonia. The mixture placed in a sealed tube was heated at 100° C. for 8 hours. After the reaction was completed, the reaction mixture was concentrated, and water was added thereto. The pH of the resulting mixture was then adjusted to 13 with 1N NaOH, and the aqueous phase was washed with ether. Subsequently, the pH of the aqueous phase was adjusted to 4 with 1N HCl. The precipitate obtained was collected by filtration, and then dried to give 114 mg of a colorless powder of the title compound (yield: 85%).

$^1$H NMR (DMSO-d$_6$) δ: 2.24 (3H, s), 2.38 (3H, s), 3.75 (3H, s), 4.84 (2H, s), 5.23 (2H, s), 6.88 (2H, d), 6.99 (1H, s), 7.17 (2H, d), 7.25 (2H, d), 7.44 (2H, d), 7.57 (1H, d), 7.58 (1H, t), 7.68 (1H, d), 7.69 (1H, t);

SIMS (m/z): 494 (M+1)$^+$

Example 39

3-Hydroxy-2,6-dimethyl-4-[2'-(tetrazol-5-yl)biphenyl-4-yl]methoxypyridine 300 mg of the compound obtained in Example 38 (a) was dissolved in a mixture of 1.5 ml of dioxane and 3 ml of methanol. To this solution was added 0.8 ml of 5N HCl, followed by stirring at 60°–70° C. for two hours. After the reaction was completed, the reaction mixture was concentrated, and water was added thereto. The resulting mixture was washed with ether. The pH of the aqueous phase was adjusted to 3.4 with 1N NaOH. The precipitate obtained was collected by filtration, and then dried to give 118 mg of a colorless powder of the title compound (yield: 78%).

$^1$H NMR (DMSO-d$_6$) δ: 2.33 (3H, s), 2.37 (3H, s), 5.24 (2H, s), 7.01 (1H, s), 7.13 (2H, d), 7.43 (2H, d), 7.52 (1H, d), 7.55 (1H, t), 7.64 (1H, t), 7.65 (1H, d);

SIMS (m/z): 374 (M+1)$^+$

Example 40

3-Ethoxycarbonyl-2,6-dimethyl-4-[2'-(tetrazol-5-yl)biphenyl-4-yl]methoxypyridine (a) The procedure described in Example 1 (a) was repeated except that the sodium hydride was replaced by potassium carbonate and the 2,6-diethyl-4(1H)-pyridone was replaced by 3-ethoxycarbonyl-2,6-dimethyl-4(1H)-pyridone, whereby 3-ethoxycarbonyl-2,6-dimethyl-4-[2'(triphenylmethyltetrazol-5-yl) biphenyl-4yl]methoxypyridine was obtained (yield: 94%).

$^1$H NMR (CDCl$_3$) δ: 1.30 (3H, t), 2.47 (3H, s), 2.51 (3H, s), 4.35 (2H, q), 5.02 (2H, s), 6.58 (1H, s), 6.19 (6H, m), 7.15 (4H), 7.19–7.33 (9H), 7.39 (1H, dd), 7.46 (1H, dt), 7.51 (1H, dt), 7.92 (1H, dd);

FDMS (m/z): 672 (M+1)$^+$ (b) The compound obtained in the step (a) was deprotected in the same manner as described in Example 1 (b), to afford a colorless powder of the title Compound (yield: 85%).

1H NMR (DMSO-d$_6$) δ: 1.21 (3H, t), 2.43 (3H, s), 2.53 (3H, s), 4.30 (2H, q), 5.31 (2H, s), 7.14 (2H, d), 7.27 (1H, s), 7.35 (2H, d), 7.56 (1H, d), 7.59 (1H, t), 7.68 (1H, d), 7.70 (1H, t);

EIMS (m/z): 429 (M$^+$)

Examples 41 to 50

The procedure in Example 40 was repeated except that the 3-ethoxycarbonyl-2,6-dimethyl-4(1H)-pyridone employed in Example 40 was replaced by various pyridones, whereby compounds of Examples 41 to 50 shown in Table 2 were respectively obtained.

TABLE 2

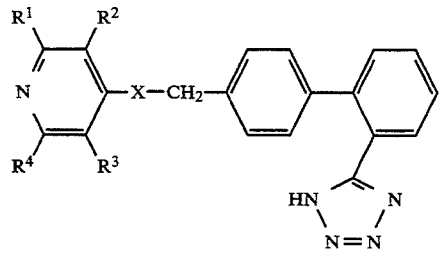

| Example | R$^1$ | R$^2$ | R$^3$ | R$^4$ | X | $^1$H NMR(DMSO-d$_6$) δ: MS(m/z): |
|---|---|---|---|---|---|---|
| 41 | CH$_3$ | CO$_2$(-i-C$_3$H$_7$) | H | CH$_3$ | O | 1.21(6H, d), 2.33(3H, s), 2.41(3H, s), 5.10(1H, m), 5.21(2H, s), 7.00(1H, s), 7.12(2H, d), 7.35(2H, d), 7.57(1H, d), 7.59 (1H, t), 7.67(1H, d), 7.70(1H, t); FDMS(m/z): 443(M+1)$^+$. |
| 42 | CH$_3$ | CO$_2$(CH$_2$)$_2$—N(2,2,6,6-tetramethylpiperidyl) | H | CH$_3$ | O | 1.41(12H, s), 1.70~1.90(6H), 2.47(3H, s), 2.52(3H, s), 3.40 (2H, t), 4.37(2H, t), 5.10(2H, s), 6.97(1H, s), 7.17(2H, d), 7.27(2H, d), 7.45(1H, t), 7.47(1H, d), 7.52(1H, t), 7.59(1H, d)*; SIMS(m/z): 569(M+1)$^+$. *CD$_3$OD |
| 43 | CH$_3$ | CO$_2$(CH$_2$)$_2$—N(piperazinyl)N—CHPh$_2$ | H | CH$_3$ | O | 2.44(4H, br. s), 2.50(3H, s), 2.54(3H, s), 2.86(4H, br. s), 2.92(2H, t), 4.14(1H, s), 4.48(2H, t), 4.92(2H, s), 6.68(1H, s), 7.11~7.33(14H, m), 7.45~7.58(3H, m), 7.91~7.94(1H, m)*; SIMS(m/z): 680(M+1)$^+$. *CDCl$_3$ |
| 44 | CH$_3$ | CO$_2$C$_2$H$_5$ | H | C$_2$H$_5$ | O | 1.21(3H, t), 1.23(3H, t), 2.36(3H, s), 2.67(2H, q), 4.28(2H, q), 5.22(2H, s), 6.96(1H, s), 7.13(2H, d), 7.35(2H, d), 7.56 (1H, d), 7.57(1H, t), 7.67(1H, d), 7.68(1H, t); SIMS(m/z): 444 (M+1)$^+$. |
| 45 | C$_2$H$_5$ | CO$_2$C$_2$H$_5$ | H | CH$_3$ | O | (a) (CDCl3) δ: 1.28(3H, t), 2.47(3H, s), 2.76(2H, q), 4.53(2H q), 5.02(2H, s), 6.57(1H, s), 6.92(6H, m), 7.14(4H, m), 7.21~ 7.33(9H), 7.39(1H, dd), 7.47(1H, dt), 7.51(1H, dt), 7.92(1H, dd); FDMS(m/z): 686(M+1)$^+$. |

TABLE 2-continued

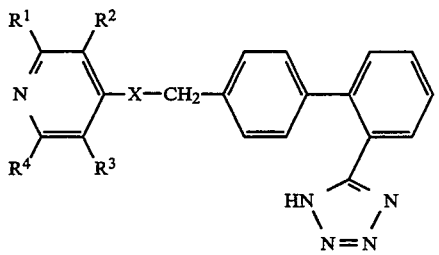

| Example | R¹ | R² | R³ | R⁴ | X | ¹H NMR(DMSO-d₆) δ:<br>MS(m/z): |
|---|---|---|---|---|---|---|
|  |  |  |  |  |  | (b) (DMSO-d₆) δ: 1.15(3H, t), 1.21(3H, t), 2.44(3H, s), 2.59 (2H, q), 4.27(2H, q), 5.21(2H, s), 6.99(1H, s), 7.13(2H, d), 7.34(2H, d), 7.57(1H, d), 7.59(1H, t), 7.67(1H, d), 7.69(1H, t); FDMS(m/z): 444(M+1)⁺. |
| 46 | C₂H₅ | CO₂CH₃ | H | CH₃ | O | 1.13(3H, t), 2.33(3H, s), 2.57(2H, q), 3.88(3H, s), 5.12(2H, s), 6.66(1H, s), 7.07(2H, d), 7.22(2H, d), 7.41(1H, d), 7.49 (1H, t), 7.56(1H, t), 7.91(1H, d)*; SIMS(m/z): 430(M+1)⁺. *CDCl₃ |
| 47 | CH₃ | CONH₂ | H | CH₃ | O | 2.35(3H, s), 2.40(3H, s), 5.17(2H, s), 6.92(1H, s), 7.12(2H, d), 7.38(2H, d), 7.50~7.76(6H); SIMS(m/z): 401(M+1)⁺. |
| 48 | CH₃ | CONHCH₃ | H | CH₃ | O | (a) (CDCl₃:CD₃OD = 5:1) δ: 2.45(3H, s), 2.47(3H, s), 2.90(3H s), 5.04(2H, s), 6.60(1H, s), 6.93(6H), 7.15(4H, s), 7.23~ 7.36(9H), 7.42(1H, dd), 7.48(1H, dt), 7.53(1H, dt), 7.90(1H, d); FDMS(m/z): 657(M+1)⁺.<br>(b) (DMSO-d₆) δ: 2.29(3H, s), 2.40(3H, s), 2.72(3H, d), 5.17 (2H, s), 6.90(1H, s), 7.12(2H, d), 7.34(2H, d), 7.58(2H, m), 7.67(1H, d), 7.68(1H, dt), 8.19(1H, q); EIMS(m/z): 414(M⁺). |
| 49 | CH₃ | CONHC₂H₅ | H | CH₃ | O | 1.03(3H, t), 2.31(3H, s), 2.41(3H, s), 3.20(2H, m), 5.17(2H, s), 6.92(1H, s), 7.11(2H, d), 7.37(2H, d), 7.56(1H, d), 7.58 (1H, t), 7.67(1H, d), 7.69(1H, t), 8.28(1H, t); FDMS(m/z): 429 (M+1)⁺. |
| 50 | CH₃ | CON⟨cyclohexyl⟩ | H | CH₃ | O | 1.30~1.65(6H), 2.28(3H, s), 2.45(3H, s), 3.10(2H, m), 3.60 (2H, m), 5.20(2H, s), 7.00(1H, s), 7.13(2H, d), 7.33(2H, d), 7.56(1H, d), 7.57(1H, t), 7.67(1H, d), 7.68(1H, t); SIMS(m/z): 469(M+1)⁺. |

(b) is of the title compound and (a) is of the precoursor, i.e., the title compound derivative where the tetrazolyl group is protected by a triphenylmethyl group.

Example 51

3-Carboxy-2,6-dimethyl-4-[2'-(tetrazol-5-yl)biphenyl-4-yl]methoxypyridine 150 mg of the compound obtained in Example 40 was dissolved in 2 ml of 1N NaOH. The solution was stirred at 60°–70° C. for 24 hours, and then cooled. The pH of the reaction mixture was adjusted to 3 with 1N HCl. The precipitate obtained was collected by filtration, washed with water, and then dried to give 84 mg of a colorless powder of the title compound (yield: 60%).

¹H NMR (DMSO-d₆) δ: 2.35 (3H, s), 2.40 (3H, s), 5.21 (2H, s), 6.97 (1H, s), 7.13 (2H, d), 7.36 (2H, d), 7.56–7.61 (2H, m), 7.65–7.71 (2H, m);

FDMS (m/z): 402 (M+1)⁺

Example 52

3-Carboxy-2-ethyl-6-methyl-4-[2'-(tetrazol-5-yl)-biphenyl-4-yl]methoxypyridine

The compound obtained in Example 45 (a) was subjected to alkaline hydrolysis in the same manner as described in Example 51, whereby the title compound was obtained (yield: 70% ).

¹H NMR (DMSO-d₆) δ: 1.19 (3H, t), 2.10 (3H, s), 2.65 (2H, q), 5.20 (2H, s), 6.93 (1H, s), 7.14 (2H, d), 7.37 (2H, d), 7.56 (1H, d), 7.57 (1H, t), 7.67 (1H, d), 7.68 (1H, t);

SIMS (m/z): 416 (M⁺)

Example 53

2,6-Dimethyl-3-(N,N-dimethylcarbamoyl)-4-[2'-(tetrazol-5-yl)bipbenyl-4-yl]methoxypyridine (a) 656 mg of the compound obtained in Example 48 (a) was dissolved in 10 ml of N,N-dimethylformamide. To this solution was added 48 mg of 60% sodium hydride, followed by stirring at room temperature for 30 minutes. Subsequently, 0.75 ml of methyl iodide was added to the mixture, followed by stirring at room temperature for four hours. Ethyl acetate was then added to the reaction mixture, and the organic phase was washed with water. Thereafter, the organic phase was dried over anhydrous magnesium sulfate, followed by concentration under reduced pressure. The residue was dissolved in 3 ml of N,N-dimethylformamide, and the reaction was repeated as described above by using 210 mg of 60% sodium hydride and 0.75 ml of methyl iodide. The residue was purified by a silica gel column chromatography (60 g, chloroform:methanol=50:1), to afford 286 mg of 2,6-dimethyl-3-(N,N-dimethylcarbamoyl)-4-[2'-( triphenylmethyltetrazol-5-yl) biphenyl-4-yl]methoxypyridine (yield: 43% ).

¹H NMR (CDCl₃) δ: 2.34 (3H, s), 2.36 (3H, s), 2.80 (3H, s), 3.09 (3H, s), 5.03 (2H, s), 6.57 (1H, s), 6.89–6.96 (6H), 7.12 (2H, d), 7.16 (2H, d), 7.21–7.35 (9H), 7.39 (1H, dd), 7.47 (1H, dt), 7.51 (1H, dt), 7.91 (1H, dd);

SIMS (m/z): 671 (M+1)⁺

(b) The compound obtained in the step (a) was deprotected in the same manner as described in Example 1

(b), whereby a colorless powder of the title compound was obtained (yield: 70%).

$^1$H NMR (DMSO-d$_6$) δ: 2.30 (3H, s), 2.48 (3H, s), 2.75 (3H, s), 2.98 (3H, s), 5.25 (2H, s), 7.11 (1H, s), 7.13 (2H, d), 7.33 (2H, d), 7.57 (1H, d), 7.58 (1H, t), 7.68 (1H, d), 7.69 (1H, t);

SIMS (m/z): 429 (M+1)+

Example 54

3-(N-Benzyl-N-methylcarbamoyl)-2,6-dimethyl-4-[2'-(tetrazol-5-yl)biphenyl-4-yl]methoxypyridine The title compound was obtained in the same manner as described in Example 53, in which benzyl bromide was reacted, instead of the methyl iodide employed in Example 53, with the compound obtained in Example 48 (a) and the protecting group of the resulting compound was removed (yield 31%).

$^1$H NMR (DMSO-d$_6$) δ: 2.26 and 2.30 (total 3H, each s), 2.41 and 2.44 (3H, s), 2.66 and 2.90 (3H, s), 4.26, 4.31, 4.46 and 4.87 (2H, d), 5.15–5.22 (2H), 6.95–7.35 (10H), 7.54–7.61 (2H), 7.65–7.71 (2H);

SIMS (m/z): 505 (M+1)+

Example 55

3-Hydroxymethyl-2,6-dimethyl-4-[2'-(tetrazol-5-yl)biphenyl-4-yl]methoxypyridine (a) 2.464 g of the compound obtained in Example 40 (a) was dissolved in 30 ml of tetrahydrofuran. To this solution was gradually added 440 mg of aluminum lithium hydride at room temperature, and the resulting mixture was refluxed for six hours. After the reaction was completed, 150 ml of ethyl acetate and 30 ml of cold water were carefully added to the reaction mixture while cooling. The mixture was stirred for 15 minutes under ice-cooling, and then stirred at room temperature for a further 30 minutes. After removing the insoluble material by filtration using "Celite" the ethyl acetate layer was washed with water, dried over anhydrous magnesium sulfate, and then concentrated under reduced pressure. The residue obtained was purified by a silica gel column chromatography (50 g, chloroform:methanol=25:1) to give 1.9 g of a light-yellow powder of 3-hydroxymethyl-2,6-dimethyl-4-[2'-(triphenylmethyl-tetrazol-5-yl)biphenyl-4-yl]methoxypyridine (yield: 79%).

$^1$H NMR (CDCl$_3$) δ: 2.48 (3H, s), 2.59 (3H, s), 4.73 (2H, s), 5.00 (2H, s), 6.60 (1H, s), 6.92 (6H, m), 7.20–7.38 (13H), 7.41 (1H, dd), 7.48 (1H, dt), 7.52 (1H, dt), 7.96 (1H, dd);

FDMS (m/z): 630 (M+1)+

(b) In a 1:1 mixture of methanol and dioxane, the compound obtained in the step (a) was deprotected using hydrochloric acid in the same manner as described in Example 1 (b), whereby a colorless powder of the title compound was obtained (yield: 48%).

$^1$H NMR (DMSO-d$_6$) δ: 2.40 (3H, s), 2.48 (3H, s), 4.52 (2H, s), 5.17 (2H, s), 6.93 (1H, s), 7.14 (2H, d), 7.40 (2H, d), 7.55 (2H, m), 7.65 (2H, m);

FDMS (m/z): 388 (M+1)+

Example 56

2-Ethyl-3-hydroxymethyl-6-methyl-4-[2'-(tetrazol-5-yl)biphenyl-4-yl]methoxypyridine (a) The compound obtained in Example 45 (a) was reduced in the same manner as described in Example 55 (a), whereby a light-yellow powder of 2-ethyl-3-hydroxymethyl-6-methyl-4-[2'-(triphenylmethyltetrazol-5-yl)biphenyl-4-yl]methoxypyridine was obtained (yield: 73%).

$^1$H NMR (CDCl$_3$) δ: 1.27 (3H, t), 2.48 (3H, s), 2.88 (2H, q), 4.73 (2H, s), 5.01 (2H, s), 6.61 (1H, s), 6.93 (6H, m), 7.17 (4H, s), 7.23–7.34 (9H), 7.41 (1H, dd), 7.48 (1H, dt), 7.52 (1H, dt), 7.95 (1H, dd);

FDMS (m/z): 644 (M+1)+

(b) The compound obtained in the step (a) was deprotected in the same manner as described in Example 55 (b), whereby a colorless powder of the title compound was obtained (yield: 64%).

1H NMR (DMSO-d$_6$) δ: 1.20 (3H, t), 2.42 (3H, s), 2.80 (2H, q), 4.54 (2H, s), 5.19 (2H, s), 6.93 (1H, s), 7.14 (2H, d), 7.42 (2H, d), 7.57 (2H, m), 7.66 (2H, m);

FDMS (m/z): 402 (M+1) +

Example 57

3-Methoxymethyl-2,6-dimethyl-4-[2'-(tetrazol-5-yl)-biphenyl-4-yl]methoxypyridine (a) 120 mg of 60% sodium hydride was suspended in 3 ml of N,N-dimethylformamide, followed by stirring at room temperature for 15 minutes. To the suspension was added a solution of 472 mg of the compound obtained in Example 55 (a) in 3 ml of N,N-dimethylformamide, followed by stirring at room temperature for 30 minutes. 94 μl of methyl iodide was added to the reaction mixture while cooling, and the mixture was stirred overnight at room temperature. After the reaction was completed, 10 ml of cold water was added to the reaction mixture, and the mixture was extracted with 120 ml of ethyl acetate. The extract was washed twice with 40 ml of a dilute saline solution, dried over anhydrous magnesium sulfate and concentrated under reduced pressure. The residue thus obtained was purified by a silica gel column chromatography (10 g, chloroform:ethyl acetate=10:1–1:1) to give 300 mg of a light-yellow powder of 3-methoxymethyl-2,6-dimethyl-4-[2'-(triphenylmethyltetrazol-5-yl)biphenyl-4yl]methoxypyridine (yield: 62%).

$^1$H NMR (CDCl$_3$) δ: 2.47 (3H, s), 2.57 (3H, s), 3.32 (3H, s), 4.53 (2H, s), 4.99 (2H, s), 6.58 (1H, s), 6.92 (6H, m), 7.15–7.35 (13H), 7.41 (1H, m), 7.49 (2H, m), 7.94 (1H, dd);

SIMS (m/z): 644 (M+1)+

(b) The compound obtained in the step (a) was deprotected in the same manner as described in Example 1 (b), whereby a colorless powder of the title compound was obtained (yield: 71%).

$^1$H NMR (DMSO-d$_6$) δ: 2.39 (3H, s), 2.43 (3H, s), 4.45 (2H, s), 5.19 (2H, s), 6.92 (1H, s), 7.14 (2H, d), 7.38 (2H, d), 7.57 (2H, t), 7.67 (2H, m);

SIMS (m/z): 402 (M+1)+

Examples 58 to 66

The procedure in Example 57 was repeated except that the methyl iodide employed in Example 57 was replaced by various alkylating agents or acylating agents, whereby compounds of Examples 58 to 66 shown in Table 3 were respectively obtained.

TABLE 3

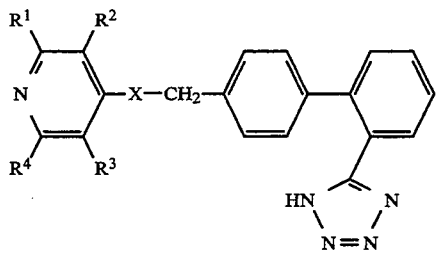

| Example | R¹ | R² | R³ | R⁴ | X | $^1$H NMR(DMSO-d$_6$) δ: MS(m/z): |
|---|---|---|---|---|---|---|
| 58 | CH$_3$ | CH$_2$OC$_2$H$_5$ | H | CH$_3$ | O | 1.09(3H, t), 2.40(3H, s), 2.44(3H, s), 3.43(2H, q), 4.48(2H, s), 5.19(2H, s), 6.91(1H, s), 7.14(2H, d), 7.38(2H, d), 7.56 (2H, dt), 7.67(2H, m); SIMS(m/z): 416(M+1)⁺. |
| 59 | CH$_3$ | CH$_2$OCH$_2$CH=CH$_2$ | H | CH$_3$ | O | 2.40(3H, s), 2.44(3H, s), 3.94(2H, d), 4.50(2H, s), 5.10(1H, s), 5.19(2H, s), 5.22(1H, d), 5.86(1H, m), 6.94(1H, s), 7.13 (2H, d), 7.38(2H, d), 7.57(2H, dt), 7.67(2H, m); SIMS(m/z): 428 (M+1)⁺. |
| 60 | CH$_3$ | CH$_2$OCH$_2$-cyclopropyl | H | CH$_3$ | O | 0.12(2H, m), 0.42(2H, m), 0.98(1H, m), 2.41(3H, s), 2.45(3H, s), 3.23(2H, d), 4.50(2H, s), 5.20(2H, s), 6.94(1H, s), 7.13 (2H, d), 7.38(2H, d), 7.56(2H, m), 7.67(2H, m); SIMS(m/z): 442 (M+1)⁺. |
| 61 | CH$_3$ | CH$_2$O(-n-C$_4$H$_9$) | H | CH$_3$ | O | 0.82(3H, t), 1.27(2H, m), 1.45(2H, m), 2.40(3H, s), 2.44(3H, s), 3.38(2H, t), 4.47(2H, s), 5.20(2H, s), 6.94(1H, s), 7.13 (2H, d), 7.38(2H, d), 7.56(2H, m), 7.66(2H, m); SIMS(m/z): 444 (M+1)⁺. |
| 62 | CH$_3$ | CH$_2$O(CH$_2$)$_2$N(CH$_3$)$_2$ | H | CH$_3$ | O | 2.41(3H, s), 2.45(3H, s), 2.57(6H, s), 3.10(2H, t), 3.60(2H, t), 4.51(2H, s), 5.11(2H, s), 6.96(1H, s), 7.14(2H, d), 7.34 (2H, d), 7.39~7.50(2H, m), 7.62(1H, d), 7.63(1H, m); SIMS(m/z): 459(M+1)⁺. |
| 63 | CH$_3$ | CH$_2$OCH$_2$CO$_2$C$_2$H$_5$ | H | CH$_3$ | O | 1.16(3H, t), 2.40(3H, s), 2.48(3H, s), 4.05(2H, ABq), 4.05(2H s), 4.63(2H, s), 5.19(2H, s), 6.90(1H, s), 7.13(2H, d), 7.39 (2H, d), 7.56(2H, m), 7.66(2H, m); SIMS(m/z): 474(M+1)⁺. |
| 64 | CH$_3$ | CH$_2$OCON(CH$_3$)$_2$ | H | CH$_3$ | O | 2.40(3H, s), 2.46(3H, s), 2.74(3H, br. s), 2.80(3H, br. s), 5.10(2H, s), 5.22(2H, s), 6.95(1H, s), 7.12(2H, d), 7.38(2H, d), 7.57(2H, dt), 7.68(2H, m); SIMS(m/z): 459(M+1)⁺. |
| 65 | CH$_3$ | CH$_2$OCOPh | H | CH$_3$ | O | 2.42(3H, s), 2.51(3H, s), 5.23(2H, s), 5.42(2H, s), 6.94(1H, s), 7.06(2H, d), 7.35(2H, d), 7.45~7.70(7H, m), 7.91(2H, d); SIMS(m/z): 492(M+1)⁺. |
| 66 | CH$_3$ | CH$_2$OCH$_2$Ph | H | CH$_3$ | O | 2.39(3H, s), 2.44(3H, s), 4.48(2H, s), 4.55(2H, s), 5.18(2H, s), 6.93(1H, s), 7.11(2H, d), 7.27~7.35(7H, m), 7.56(2H, m), 7.68(2H, m); SIMS(m/z): 478(M+1)⁺. |

Example 67

3-Acetoxymethyl-2,6-dimethyl-4-[2'-(tetrazol-5-yl)-biphenyl-4-yl]methoxypyridine (a) 850 mg of the compound obtained in Example 55 (a) was dissolved in 2 ml of pyridine. To this solution was added 1 ml of acetic anhydride under ice-cooling, and the mixture was stirred overnight at room temperature. After the reaction was completed, 20 ml of ice water was added to the mixture, followed by extraction with 300 ml of ethyl acetate. The extract was washed with a saturated saline solution, a saturated aqueous solution of sodium hydrogencarbonate and a saturated saline solution successively, dried over anhydrous magnesium sulfate and then concentrated under reduced pressure. The residue thus obtained was washed with 50 ml of diethyl ether, and then dried to give 715 mg of a colorless powder of 3-acetoxymethyl-2,6-dimethyl-4-[2'-(triphenylmethyltetrazol-5-yl)biphenyl-4yl]methoxypyridine (yield: 79%).

$^1$H NMR (CDCl$_3$) δ: 2.02 (3H, s), 2.47 (3H, s), 2.54 (3H, s), 5.02 (2H, s), 5.23 (2H, s), 6.59 (1H, s), 6.91 (6H, d), 7.16 (4H, s), 7.21–7.34 (9H), 7.40 (1H, dd), 7.49 (2H, m), 7.94 (1H, m);

FDMS (m/z): 672 (M+1)⁺

(b) 210 mg of the compound obtained in the step (a) was deprotected in the same manner as described in Example 1 (b). After the reaction was completed, 5 ml of water was added to the reaction mixture while cooling with ice, and the pH of the mixture was adjusted to 6.8–7.0 with 1N NaOH, followed by washing with 30 ml of diethyl ether. The precipitate was collected by filtration, washed with cold water and diethyl ether and then dried to give 80 mg of a colorless crystalline powder of the title compound (yield: 60%).

$^1$H NMR (DMSO-d$_6$) δ: 1.99 (3H, s), 2.40 (3H, s), 2.44 (3H, s), 5.13 (2H, s), 5.21 (2H, s), 6.92 (1H, s), 7.13 (2H, d)., 7.38 (2H, d), 7.57 (2H, dt), 7.67 (2H, m);

SIMS (m/z): 430 (M+1)⁺

Example 68

3-Formyl-2,6-dimethyl-4-[2'-(tetrazol-5-yl)biphenyl-4-yl]methoxypyridine (a) 944 mg of the compound obtained in Example 55 (a) was dissolved in 12 ml of methylene chloride. To this solution was added 565 mg of pyridinium chlorochromate while cooling, followed by stirring at room temperature for three hours.

After the reaction was completed, the reaction mixture was cooled, and 50 ml of ethyl acetate was added thereto. An insoluble material was removed from the mixture by filtration, and was washed several times with 50 ml of ethyl acetate. The ethyl acetate layer was washed with a saturated aqueous solution of sodium hydrogencarbonate and a dilute saline solution, dried over anhydrous magnesium sulfate, and then evaporated under reduced pressure. The residue thus obtained was purified by a silica gel column chromatography (30 g, chloroform:ethyl acetate=50:1) to give 410 mg of a light-yellow powder of 3-formyl-2,6-dimethyl-4-[2'-(triphenylmethyltetrazol-5-yl)biphenyl-4yl]methoxypyridine-(yield: 44%).

$^1$H NMR (CDCl$_3$) δ: 2.53 (3H, s), 2.76 (3H, s), 5.08 (2H, s), 6.72 (1H, s), 6.91 (6H, m), 7.15–7.25 (10H), 7.32 (3H, m), 7.40 (1H, dd), 7.50 (2H, m), 7.98 (1H, dd);
SIMS (m/z): 628 (M+1)$^+$ (b) 400 mg of the compound obtained in the step (a) was deprotected in the same manner as described in Example 1 (b), whereby 175 mg of a colorless powder of the title compound was obtained (yield: 71%).

$^1$H NMR (DMSO-d$_6$) δ: 2.47 (3H, s), 2.61 (3H, s), 5.31 (2H, s), 7.15 (2H, d), 7.16 (1H, s), 7.45 (2H, d), 7.59 (2H, dt), 7.69 (2H, m), 10.51 (1H, s);
EIMS (m/z): 383 (M-2)$^+$

Example 69

3-Amino-2,6-dimethyl-4-[2'-(tetrazol-5-yl)biphenyl-4-yl]methoxypyridine 400 mg of the compound obtained in Example 29 was suspended in a mixture of 12 ml of methanol and 1 ml of acetic acid. To this suspension were added 400 mg of iron powder and then 0.4 ml of 5N HCl, followed by stirring at 80° C. for five hours. An insoluble material was removed from the mixture by filtration using, "Celite", and the filtrate was concentrated under reduced pressure. Water was added to the concentrated reaction mixture, and the pH of the mixture was adjusted to 14 with 1N NaOH. The insoluble material was then removed by filtration using "Celite". The filtrate was charged on 50 ml of "HP-20" resin, washed with water and then eluted with a 30% aqueous acetone solution to obtain the desired compound. The eluate was concentrated under reduced pressure, and the precipitate was dried, whereby 367 mg of the title compound was obtained (yield: 95%).

$^1$H NMR (CD$_3$OD) δ: 2.44 (3H, s), 2.49 (3H, s), 5.31 (2H, s), 7.07 (1H, s), 7.16 (2H, d), 7.30 (2H, d), 7.40–7.45 (2H), 7.50 (1H, t), 7.58 (1H, d);
SIMS (m/z): 373 (M+1)$^+$

Example 70

3-Acetylamino-2,6-dimethyl-4-[2'-(tetrazol-5-yl)biphenyl-4-yl]methoxypyridine

To a solution of 100 mg of the compound obtained in Example 69 placed in 2 ml of pyridine was added 1 ml of acetic anhydride, followed by stirring at 60° C. for three hours. After the reaction was completed, the reaction mixture was concentrated under reduced pressure. The residue was purified by a silica gel column chromatography (8 g, chloroform:methanol=2:1), whereby 95 mg of a colorless powder of the title compound was obtained (yield: 86%).

$^1$H NMR (CD$_3$OD) δ: 2.13 (3H, s), 2.39 (3H, s), 2.50 (3H, s), 5.20 (2H, s), 6.99 (1H, s), 7.15 (2H, d), 7.31 (2H, d), 7.47 (1H, t), 7.49 (1H, t), 7.55 (1H, t), 7.59 (1H, d);
SIMS (m/z): 415 (M+1)$^+$

Example 71

2-Methyl-4-[2'-(tetrazol-5-yl)biphenyl-4-yl]-methoxypyridine (a) 240 mg of 60% sodium hydride was suspended in 4 ml of N,N-dimethylformamide, followed by stirring at room temperature for 20 minutes. To this suspension was added a solution of 545 mg of 2-methyl-4(1H)-pyridone in 6 ml of N,N-dimethylformamide, and the resulting mixture was stirred at room temperature for 30 minutes. Subsequently, a solution of 3.07 g of 4'-bromomethyl-2-(triphenylmethyltetrazol-5-yl)biphenyl in 12 ml of N,N-dimethylformamide was added to the reaction mixture, followed by stirring at 60° C. for four hours. After the reaction was completed, the mixture was cooled to room temperature, to which was added 50 ml of cold water. The mixture was extracted twice with 150 ml of ethyl acetate. The extract was washed with a saturated aqueous solution of sodium hydrogencarbonate, water and a saline solution successively, dried over anhydrous magnesium sulfate, and then evaporated under reduced pressure. The residue thus obtained was purified by a silica gel column chromatography (100 g) to give two components. Namely, from the eluate of chloroform and ethyl acetate in the ratio of 25:1, 1.0 g of a light-yellow oily product of 2-methyl-4-[2'-(triphenylmethyltetrazol-5-yl)biphenyl-4-yl ]methoxypyridine was obtained (yield: 34% ).

$^1$H NMR (CDCl$_3$ ) δ: 2.51 (3H, s), 4.96 (2H, s), 6.66 (1H, dd), 6.72 (1H, d), 6.91 (6H, br. d), 7.22–7.34 (13H), 7.40 (1H, dd), 7.49 (2H, m), 7.96 (1H, dd), 8.30 (1H, d);
FDMS (m/z): 586 (M+1)$^+$ (b) The eluate of chloroform and ethyl acetate in the ratio of 20:1 to 5: 1, obtained by the above chromatographic purification in the step (a), afforded 1.52 g of a white powder of 2-methyl-1-[2'-(triphenylmethyltetrazol-5-yl)biphenyl-4-yl]methyl-4(1H)-pyridone (yield: 52%).

$^1$H NMR (CDCl$_3$) δ: 2.09 (3H, s), 4.86 (2H, s), 6.32 (2H, m), 6.78 (2H, br. d), 6.90 (6H, m), 7.15 (2H, m), 7.23–7.28 (11H), 7.35 (2H, m), 7.50 (2H, m), 7.99 (1H, dd);
FDMS (m/z): 586 (M+1)$^+$ (c) 880 mg of the compound obtained in the step (a) was dissolved in a mixture solvent of 1 ml of methylene chloride and 8 ml of methanol. To this solution was added 0.6 ml of 4N HCl while cooling with ice, followed by stirring at 10°–15° C. for one hour. After the reaction was completed, the reaction mixture was treated in the same manner as described in Example 1 (b), whereby 266 mg of a colorless powder of the title compound was obtained (yield: 52%).

$^1$H NMR (DMSO-d$_6$) δ: 2.42 (3H, s), 5.16 (2H, s), 6.87 (1H, dd), 6.94 (1H, d), 7.13 (2H, d), 7.39 (2H, d), 7.56 (2H, m), 7.67 (2H, m), 8.26 (1H, d);
EIMS (m/z): 343 (M$^+$)

Example 72

2-Methyl-1-[2'-(tetrazol-5-yl)biphenyl-4-yl]methyl-4(1H)-pyridone 1.11 g of the compound obtained in Example 71 (b) was deprotected in the same manner as described in Example 71 (c), whereby 371 mg of a colorless powder of the title compound was obtained (yield: 57%).

$^1$H NMR (DMSO-d$_6$ ) δ: 2.17 (3H, s), 5.20 (2H, s), 6.12 (1H, s), 6.14 (1H, d), 7.05 (2H, d), 7.12 (2H, d), 7.51–7.59 (2H, m), 7.67 (2H, m), 7.83 (1H, d);

FDMS (m/z): 344 (M+1) +

The procedure in Example 71 was repeated except that the 2-methyl-4(1H)-pyridone employed in Example 71 was replaced by 3-methoxy-2-methyl-4(1H)-pyridone, thereby obtaining the following two compounds of Examples 73 and 74.

Example 73

3-Methoxy-2-methyl-4-[2'-(tetrazol-5-yl)biphenyl-4-yl]methoxypyridine colorless powder $^1$H NMR (DMSO-d$_6$) δ: 2.16 (3H, s), 3.70 (3H, s), 5.23 (2H, s), 6.19 (1H, d), 7.03 (2H, d), 7.11 (1H, d), 7.52–7.59 (2H, m), 7.66 (2H, m), 7.77 (1H, d);
FDMS (m/z ): 374 (M+1)+

Example 74

3-Methoxy-2-methyl-1-[2'-(tetrazol-5-yl)biphenyl-4-yl]methyl-4(1H)-pyridone colorless crystalline product $^1$H NMR (DMSO-d$_6$) δ: 2.38 (3H, s), 3.75 (3H, s), 5.21 (2H, s), 7.04 (1H, d), 7.14 (2H, d), 7.42 (2H, d), 7.55–7.60 (2H, m), 7.65–7.70 (2H, m), 8.07 (1H, d);
FDMS (m/z ): 374 (M+1)+

The procedure in Example 71 was repeated except that the 2-methyl-4(1H)-pyridone employed in Example 71 was replaced by 5-methoxy-2-methyl-4(1H-)-pyridone, thereby obtaining the following two compounds of Examples 75 and 76.

Example 75

5-Methoxy-2-methyl-4-[2'-(tetrazol-5-yl)biphenyl-4-yl]methoxypyridine colorless powder $^1$H NMR (DMSO-d$_6$) δ: 2.33 (3H, s), 3.82 (3H, s), 5.10 (2H, s), 6.78 (1H, s), 7.01 (2H, d), 7.15 (2H, d), 7.37 (1H, d), 7.46 (1H, t), 7.52 (1H, t), 7.73 (1H, s), 7.81 (1H, d);
FDMS (m/z): 374 (M+1)+

Example 76

5-Methoxy-2-methyl-1-[2'-(tetrazol-5-yl)biphenyl-4-yl]methyl-4-(1H)-pyridone colorless crystalline product $^1$H NMR (DMSO-d$_6$) δ: 2.13 (3H, s), 3.58 (3H, s), 5.20 (2H, s), 6.10 (1H, s), 7.03 (2H, d), 7.09 (2H, d), 7.51–7.70 (4H, m), 8.32 (1H, s);
FDMS (m/z): 374 (M+1)+

Example 77

2,6-Dimethyl-4-[2'-(tetrazol-5-yl)biphenyl-4-yl]methoxypyridine (a) 369 mg of 2,6-dimethyl-4(1H)-pyridone was dissolved in 5 ml of N,N-dimethylformamide. To this solution was added 144 mg of 60% sodium hydride, followed by stirring at room temperature for 15 minutes. Subsequently, 900 mg of 4-bromomethyl-2'-cyanobiphenyl was added to the mixture, and the mixture was stirred at room temperature for two hours. After the reaction was completed, ethyl acetate was added to the reaction mixture, and the mixture was washed with water and dried over anhydrous magnesium sulfate. The organic layer was concentrated under reduced pressure, to which was added ethyl acetate. The precipitated crystals were collected by filtration and then dried, and, on the other hand, the filtrate was purified by a silica gel column chromatography (80 g, chloroform:ethyl acetate=3:1 to 2:3), whereby 296 mg and 329 mg of 2,6-dimethyl-4-(2'-cyanobiphenyl-4-yl)methoxypyridine were obtained, respectively (total amount: 625 mg, yield: 66%).

$^1$H NMR (CDCl$_3$) δ: 2.50 (6H, s), 5.15 (2H, s), 6.61 (2H, s), 7.47 (1H, dt), 7.53 (1H, dd), 7.54 (2H, d), 7.60 (2H, d), 7.66 (1H, dt), 7.78 (1H, dd);
EIMS (m/z): 314 (M+)

(b) 575 mg of the compound obtained in the step (a) was dissolved in 10 ml of toluene. To this solution were added 475 mg of sodium azide and 2 ml of tri-(n-butyl)-tin chloride, followed by stirring at 120° C. for three days. Subsequently, 0.22 ml of 10N NaOH and 622 mg of tritylchloride were added to the reaction mixture while cooling, and the mixture was stirred at 60° C. for 10 hours. Ethyl acetate was added to the reaction mixture, and the organic layer was washed with water, dried over anhydrous magnesium sulfate and then concentrated under reduced pressure. Since it was found that the starting material was remaining in the residue, 10 ml of dioxane and 0.5 ml of 10N NaOH were added to the residue, followed by stirring at room temperature for 30 minutes. 1 g of tritylchloride was then added to the mixture for further reaction. After the reaction was completed, ethyl acetate and water were added to the reaction mixture, and an insoluble material was removed by filtration using "Celite". The aqueous phase of the filtrate was extracted with ethyl acetate. The extract and the ethyl acetate phase of the filtrate were mixed, and the mixture was dried over anhydrous magnesium sulfate, followed by concentration under reduced pressure. The residue thus obtained was purified by a silica gel column chromatography (70 g, chloroform:ethyl acetate=3:1) to give 759 mg of 2,6-dimethyl-4-[2'-( triphenylmethyltetrazol-5-yl)biphenyl-4-yl]methoxypyridine (yield: 69% ).

$^1$H NMR (CDCl$_3$) δ: 2.47 (6H, s), 4.94 (2H, s), 6.54 (2H, s), 6.91 (2H, d), 6.91 (4H, m), 7.22–7.34 (12H), 7.40 (1H, dd), 7.49 (1H, m), 7.95 (1H, dd), 8.02 (2H, br. s);
FDMS (m/z): 600 (M+1)+

The above NMR data agreed with the NMR data concerning the precursor (compound containing a tetrazole group protected by a triphenylmethyl group) of the compound obtained in Example 2.

(c) The compound obtained in the step (b) was deprotected in the same manner as described in Example 1 (b) to give the title compound (yield: 78%). The spectral data concerning this compound agreed with the data regarding the compound obtained in Example 2. It was therefore confirmed that this compound was identical with the compound obtained in Example 2.

Example 78

2,6-Dimethyl-4-(2'-carboxybiphenyl-4-yl)methoxypyridine (a) 96 mg of 60% sodium hydride was suspended in 2 ml of dried N,N-dimethylformamide, followed by stirring at room temperature for 20 minutes. To this suspension was added 246 mg of 2,6-dimethyl-4(1H)-pyridone, and the mixture was stirred for a further 30 minutes. Subsequently, to this reaction mixture was added a solution of 732 mg of methyl 4'-bromomethylbiphenyl-2-carboxylate in 4 ml of dried N,N-dimethylformamide, followed by stirring at room temperature for four hours and then at 60° C. for 30 minutes. After the reaction was completed, the reaction mixture was cooled to room temperature, to which was added 40 ml of cold water. The mixture was extracted twice with 100 ml of ethyl acetate. The extract was washed with a saline solution, dried over anhydrous magnesium sulfate and then evaporated under reduced pressure. The residue was purified by a silica gel column chromatography, whereby 540 mg of a light-yellow oily product of 2,6-dimethyl-4-(2'-methoxycarbonylbiphenyl-4-yl)methoxypyridine was obtained (yield: 78%).

$^1$H NMR (CDCl$_3$) δ: 2.48 (6H, s), 3.65 (3H, s), 5.12 (2H, s), 6.60 (2H, s), 7.34–7.46 (6H, m), 7.54 (1H, dt), 7.85 (1H, d);

EIMS (m/z): 347 (M$^+$)

(b) 350 mg of the compound obtained in the step (a) was dissolved in 10 ml of ethanol. To this solution was added 1.0 ml of 5N NaOH, followed by stirring at 60° C. for one hour. After the reaction was completed, the reaction mixture was concentrated and dried up under reduced pressure. 5 ml of cold water was added to the residue for dissolution. The aqueous solution thus obtained was washed with 20 ml of ethyl acetate, and the pH of the solution was then adjusted to 3 with 5N HCl under ice cooling. The precipitate was collected by filtration, washed with water and then dried overnight at 40° C. under reduced pressure to give 290 mg of a colorless crystalline product of the title compound (yield: 87%).

$^1$H NMR (DMSO-d$_6$) δ: 2.64 (6H, s), 5.42 (2H, s), 7.40 (2H, d), 7.40 (1H, d), 7.41 (2H, s), 7.48 (1H, dt), 7.53 (2H, d), 7.59 (1H, dt), 7.76 (1H, d);

FDMS (m/z): 334 (M+1)$^+$

Examples 79 to 90

Compounds of Examples 79 to 90 shown in Table 4 were obtained in the same manner as described in Examples 78, in which various pyridones were reacted, instead of the 2,6-dimethyl-4(1H)-pyridone employed in Example 78, with methyl 4'-bromomethylbiphenyl-2-carboxylate, followed by deesterification.

TABLE 4

| Example | R$^1$ | R$^2$ | R$^3$ | R$^4$ | X | $^1$H NMR(DMSO-d$_6$) δ: MS(m/z): |
|---------|-------|-------|-------|-------|---|------|
| 79 | CH$_3$ | H | H | C$_2$H$_5$ | O | 1.27(3H, t), 2.54(3H, s), 2.81(2H, q), 5.32(2H, s), 7.10(1H, br. s), 7.13(1H, br. s), 7.38(2H, d), 7.38(1H, d), 7.47(1H, t) 7.51(2H, d), 7.58(1H, t), 7.75(1H, d); FDMS(m/z): 348(M+1)$^+$. |
| 80 | CH$_3$ | H | H | n-C$_4$H$_9$ | O | 0.90(3H, t), 1.32(2H, m), 1.62(2H, m), 2.39(3H, s), 2.61(2H, t), 5.17(2H, s), 6.71(1H, br. s), 6.75(1H, br. s), 7.37(3H, m) 7.46(3H, m), 7.57(1H, t), 7.74(1H, d); FDMS(m/z): 376(M+1)$^+$. |
| 81 | C$_2$H$_5$ | H | H | C$_2$H$_5$ | O | 1.24(6H, t), 2.75(4H, q), 5.28(2H, s), 7.00(2H, s), 7.37(2H, d), d), 7.47(1H, t), 7.51(1H, t), 7.58(1H, t), 7.74(1H, d); FDMS 7.39(1H, (M+1)$^+$. |
| 82 | CH$_3$ | OCH$_3$ | H | CH$_3$ | O | 2.32(3H, s), 2.36(3H, s), 3.72(3H, s), 5.22(2H, s), 6.99(1H, s), 7.38(2H, d), 7.41(1H, dd), 7.47(1H, dt), 7.51(2H, d), 7.59 (1H, dt), 7.74(1H, dd); EIMS(m/z): 363(M+1)$^+$. |
| 83 | CH$_3$ | OC$_2$H$_5$ | H | CH$_3$ | O | 1.26(3H, t), 2.32(3H, s), 2.34(3H, s), 3.96(2H, q), 5.21(2H, s), 6.95(1H, s), 7.37(2H, d), 7.40(1H, dd), 7.45(1H, dt), 7.49 (2H, d), 7.57(1H, dt), 7.73(1H, dd); EIMS(m/z): 377(M+1)$^+$. |
| 84 | CH$_3$ | H | H | CH$_3$ | S | 2.39(6H, s), 4.40(2H, s), 7.10(2H, br. s), 7.30(2H, d), 7.39 (1H, d), 7.44(1H, dt), 7.46(2H, d), 7.57(1H, dt), 7.72(1H, dd); FDMS(m/z): 350(M+1)$^+$. |
| 85 | H | H | H | H | S | 4.29(2H, s), 7.18(2H, dd), 7.32~7.44(6H, m), 7.51(1H, dt), 7.81(1H, dd), 8.37(2H, dd)*; FDMS(m/z): 322(M+1)$^+$. *DMSO-d$_6$:CDCl$_3$ = 1:1 |
| 86 | —(CH$_2$)$_3$— | | H | H | S | 2.05(2H, m), 2.74(2H, t), 2.90(2H, t), 4.40(2H, s), 7.17(1H, d), 7.31(2H, d), 7.37(1H, d), 7.44(1H, d), 7.47(2H, d), 7.56 (1H, t), 7.72(1H, d), 8.17(1H, d); FDMS(m/z): 362(M+1)$^+$. |
| 87 | —(CH$_2$)$_3$— | | Br | H | S | 2.01(2H, m), 2.80(2H, t), 2.92(2H, t), 4.15(2H, s), 7.15(2H, d), 7.25(2H, d), 7.28(1H, dd), 7.39(1H, dt), 7.50(1H, dt), 7.81(1H, dd), 8.46(1H, br. s)*; FDMS(m/z): 441(M+1)$^+$. *DMSO-d$_6$:CDCl$_3$ = 1:1 |
| 88 | (pyridine-thiol structure) | | | | | 4.46(2H, s), 7.03(1H, m), 7.13~7.45(7H, m), 7.47~7.60(2H, m) 7.73(1H), 8.45(1H, t)*; EIMS(m/z): 321(M$^+$). *DMSO-d$_6$:CDCl$_3$ = 1:1 |
| 89 | CH$_2$OH-pyridone structure | | | | | 4.49(2H, d), 5.21(2H, s), 5.28(1H, t), 7.36(2H, d), 7.39(2H, d), 7.43~7.54(4H, m), 7.58(1H, t), 7.73(1H, d), 8.28(1H, d), 12.76(1H, br. s); FDMS(m/z): 336(M+1)$^+$. |

TABLE 4-continued

| | | | A | | | ¹H NMR(DMSO-d₆) δ: |
|---------|----|----|----|----|---|---------|
| Example | R¹ | R² | R³ | R⁴ | X | MS(m/z): |
| 90 | O= ⟨ring⟩ N— | | | | | 5.07(2H, s), 6.37(2H, d), 7.23(2H, d), 7.30~7.60(6H, m), 7.88 (2H, d)*; EIMS(m/z): 305(M⁺). *DMSO-d₆:CDCl₃ = 1:1 |

Example 91

2,3-Dimethyl-4-(2'-carboxybiphenyl-4-yl)methoxypyridine (a) 96 mg of 60% sodium hydride was suspended in 2 ml of dried N,N-dimethylformamide, followed by stirring at room temperature for 20 minutes. To this suspension was added 246 mg of 2,3-dimethyl-4(1H)-pyridone, and the mixture was stirred for a further 30 minutes. Subsequently, a solution of 732 mg of methyl 4'-bromomethylbiphenyl-2-carboxylate in 4 ml of dried N,N-dimethylformamide was added to the reaction mixture, followed by stirring at room temperature for four hours and then at 60° C. for 30 minutes. After the reaction was completed, the reaction mixture was cooled to room temperature, to which was added 40 ml of cold water. The resulting mixture was extracted twice with 100 ml of ethyl acetate. The extract was washed with a saline solution, dried over anhydrous magnesium sulfate and evaporated under reduced pressure. The residue was purified by a silica gel column chromatography to give two components. Namely, 170 mg of a light-yellow oily product of 2,3-dimethyl-4-(2'-methoxycarbonylbiphenyl-4-yl)methoxypyridine was obtained from the eluate of chloroform and ethyl acetate in the ratio of 25:1 and the eluate of chloroform and methanol in the ratio of 50:1 (yield: 25%).

¹H NMR (CDCl₃) δ: 2.22 (3H, s), 2.51 (3H, s), 3.64 (3H, s), 5.16 (2H, s), 6.71 (1H, d), 7.32–7.50 (6H, m), 7.54 (1H, dt), 7.85 (1H, dd), 8.23 (1H, d);

EIMS (m/z): 347 (M⁺)

(b) The eluate of chloroform and methanol in the ratio of 5:1, obtained by the chromatographic purification in the step (a), afforded 380 mg of a white powder of 2,3-dimethyl-4-(2'-methoxycarbonylbiphenyl-4-yl)methyl-4(1H)-pyridone (yield: 55%).

¹H NMR (CDCl₃) δ: 2.21 (3H, s), 2.26 (3H, s), 3.68 (3H, s), 5.10 (2H, s), 6.40 (1H, d), 7.06 (2H, d), 7.30–7.37 (4H, m), 7.43 (1H, dt), 7.54 (1H, dt), 7.87 (1H, dd);

EIMS (m/z): 347 (M⁺)

(c) 153 mg of the compound obtained in the step (a) was dissolved in 4 ml of ethanol, to which was added 0.44 ml of 5N NaOH, followed by stirring at 60° C. for 3 to 4 hours. After the reaction was completed, the reaction mixture was concentrated and dried up under reduced pressure. 4 ml of water was added to the residue for dissolution. The aqueous solution was washed with 10 ml of ethyl acetate, and the pH of the solution was adjusted to 3–4 with 5N HCl while cooling with ice. The precipitate was collected by filtration, washed with water, and then dried overnight at 40° C. under reduced pressure to give 140 mg of a colorless crystalline product of the title compound (yield: 96%).

¹H NMR (DMSO-d₆) δ: 2.22 (3H, s), 2.64 (3H, s), 5.51 (2H, s), 7.40 (2H, d), 7.40 (1H, d), 7.48 (1H, t), 7.54 (2H, d), 7.58 (1H, d), 7.59 (1H, t), 7.75 (1H, d), 8.60 (1H, d), 12.80 (1H, br. s);

FDMS (m/z): 334 (M+1)⁺

Example 92

2,3-Dimethyl-1-(2'-carboxybiphenyl-4-yl)methyl-4(1H)-pyridone 350 mg of the compound obtained in Example 91 (b) was deprotected in the same manner as described in Example 91 (c), whereby 290 mg of a colorless crystalline product of the title compound was obtained (yield: 87%).

¹H NMR (DMSO-d₆) δ: 1.91 (3H, s), 2.19 (3H, s), 5.27 (2H, s), 6.10 (1H, d), 7.11 (2H, d), 7.35 (2H, d), 7.36 (1H, d), 7.44 (1H, t), 7.55 (1H, t), 7.70 (1H, d), 7.81 (1H, d);

EIMS (m/z): 333 (M⁺)

The procedure in Example 91 was repeated except that the 2,3-dimethyl-4 (1H)-pyridone was replaced by 2,3-cyclopenteno-4(1H)-pyridone, whereby the following two compounds of Examples 93 and 94 were obtained.

Example 93

2,3-Cyclopenteno-4-(2'-carboxybiphenyl-4-yl)methoxypyridine light-yellow crystalline product ¹H NMR (CDCl₃) δ: 2.10 (2H, m), 2.90 (2H, t), 2.98 (2H, t), 5.20 (2H, s), 6.67 (1H, d), 7.31–7.44 (6H, m), 7.4S (1H, dt), 7.88 (1H, d), 8.08 (1H, d);

FDMS (m/z): 346 (M+1)⁺

Example 94

2,3-Cyclopenteno-1-(2'-carboxybiphenyl-4-yl)methyl-4(1H-)-pyridone colorless crystalline product ¹H NMR (DMSO-d₆) δ: 1.93 (2H, m), 2.61 (2H, t), 2.87 (2H, t), 5.17 (2H, s), 6.07 (1H, d), 7.20 (2H, d), 7.32–7.37 (3H, m), 7.44 (1H, t), 7.55 (1H, t), 7.72 (1H, d), 7.75 (1H, d);

FDMS (m/z): 346 (M+1)⁺

The procedure in Example 91 was repeated except that the 2,3-dimethyl-4 (1H) -pyridone was replaced by 3-benzyloxy-2-methyl-4(1H)-pyridone, whereby the following two compounds of Examples 95 and 96 were obtained.

Example 95

3-Benzyloxy-2-methyl-4-(2'-carboxybiphenyl-4-yl)methoxypyridine colorless crystalline product $^1$H NMR (DMSO-d$_6$) δ: 2.78 (3H, s), 5.11 (2H, s), 5.56 (2H, s), 7.38 (8H, m), 7.48 (1H, t), 7.52 (3H, t), 7.71 (1H, q), 7.76 (1H, d), 8.52 (1H, d);

FDMS (m/z): 425 (M+)

Example 96

3-Benzyloxy-2-methyl-1-(2'-carboxybiphenyl-4-yl)methyl-4(1H-)-pyridone colorless crystalline product $^1$H NMR (DMSO-d$_6$) δ: 2.02 (3H, s), 5.07 (2H, s), 5.23 (2H, s), 6.25 (1H, d), 6.99 (1H, d), 7.34 (8H, m), 7.46 (1H, t), 7.58 (1H, t), 7.73 (1H, d), 7.79 (1H, d);

FDMS (m/z): 426 (M+1)+

The procedure in Example 91 was repeated except that the 2,3-dimethyl-4(1H)-pyridone was replaced by 2-hydroxymethyl-5-(p-methoxybenzyloxy)-4(1H)-pyridone, whereby the following two compounds of Examples 97 and 98 were obtained.

Example 97

2-Hydroxymethyl-5-(p-methoxybenzyloxy)-4-(2'-carboxybiphenyl-4-yl)methoxypyridine colorless powder $^1$H NMR (CDCl$_3$: CD$_3$OD=10:1) δ: 3.81 (3H, s), 4.62 (2H, s), 5.13 (2H, s), 5.32 (2H, s), 6.90 (2H, d), 7.12 (1H, s), 7.36 (2H, d), 7.39 (1H, d), 7.34–7.47 (8H, m), 7.54 (1H, dt), 7.88 (1H, dd), 8.04 (1H, s);

EIMS (m/z): 471 (M+)

Example 98

2-Hydroxymethyl-5-(p-methoxybenzyloxy)-1-(2'-carboxybiphenyl-4-yl)methyl-4(1H)-pyridone colorless powder $^1$H NMR (CDCl$_3$: CD$_3$OD=10:1) δ: 3.85 (3H, s), 4.40 (2H, s), 5.06 (2H, s), 5.19 (2H, s), 6.55 (1H, s), 6.85 (2H, d), 6.94 (2H, d), 7.15 (1H, s), 7.28 (2H, s), 7.31 (2H, d), 7.33 (1H, d), 7.44 (1H, dd), 7.55 (1H, dd), 7.91 (1H, d);

FDMS (m/z): 472 (M+1)+

Example 99

5-Hydroxy-2-hydroxymethyl-4-(2'-carboxybiphenyl-4-yl)methoxypyridine 95 mg of the compound obtained in Example 97 was suspended in 0.3 ml of anisole, to which was added 0.5 ml of trifluoroacetic acid under ice cooling, followed by stirring at the temperature for approximately one hour. After the reaction was completed, the reaction mixture was poured into 20 ml of cooled isopropyl ether to form a precipitate. The precipitate obtained was collected by filtration, and then dried overnight at 40° C. under reduced pressure, whereby 85 mg of a colorless powder of the title compound was obtained as a trifluoroacetate.

$^1$H NMR (DMSO-d$_6$) δ: 4.66 (2H, s), 5.38 (2H, s), 7.40 (2H, d), 7.41 (1H, s), 7.47 (1H, dd), 7.56 (2H, d), 7.51–7.61 (2H, m), 7.76 (1H, d), 8.02 (1H, s);

SIMS (m/z): 352 (M+1)+

Example 100

5-Hydroxy-2-hydroxymethyl-(2'-carboxybiphenyl-4-yl)methyl-4(1H)-pyridone

The compound obtained in Example 98 was removed the p-methoxybenzyl group contained therein, using trifluoroacetic acid, in the same manner as described in Example 99, whereby a colorless powder of the title compound was obtained.

$^1$H NMR (DMSO-d$_6$) δ: 4.48 (2H, s), 5.41 (2H, s), 6.81 (1H, s), 7.19 (2H, d), 7.36 (2H, d), 7.37 (1H, d), 7.46 (1H, dd), 7.57 (1H, dd), 7.74 (1H, d), 7.88 (1H, s);

FDMS (m/z): 352 (M+1)+

Example 101

3-Ethoxycarbonyl-2,6-dimethyl-4-(2'-carboxybiphenyl-4-yl)methoxypyridine (a) 349 mg of 60% sodium hydride was suspended in 20 ml of dried N,N-dimethylformamide. To this suspension was added a solution of 154 mg of 3-ethoxycarbonyl-2,6-dimethyl-4(1H)-pyridone in 5 ml of N,N-dimethylformamide while cooling with ice, followed by stirring at room temperature for 20 minutes. Subsequently, a solution of 3.01 g of tert-butyl- 4'-bromomethylbiphenyl-2carboxylate in 5 ml of N,N-dimethylformamide was added to the above mixture, followed by stirring at room temperature for a further three hours. After the reaction was completed, the solvent was removed from the mixture under reduced pressure, to which was added 50 ml of water. The mixture was extracted three times with 70 ml of ethyl acetate. The extract was washed with a saturated saline solution, dried over anhydrous magnesium sulfate and evaporated the solvent under reduced pressure. The residue was purified by a silica gel column chromatography (n-hexane:ethyl acetate=1:2) to give 2.18 g of 3-ethoxycarbonyl-2,6-dimethyl-4-(2'-tert-buthoxycarbonylbiphenyl-4-yl)methoxypyridine (yield: 60%).

$^1$H NMR (CDCl$_3$) δ: 1.22 (9H, s), 1.35 (3H, t), 2.49 (6H, s), 4.38 (2H, q), 5.20 (2H, s), 6.64 (1H, s), 7.28–7.53 (7H, m), 7.77–7.82 (1H, m);

SIMS (m/z): 462 (M+1)+

(b) 461 mg of the compound obtained in the step (a) was added to a mixture of 3 ml of formic acid and 2 ml of 1N HCl, followed by stirring at room temperature for 12 hours. After removing the solvent, 20 ml of a 6% aqueous solution of sodium hydrogencarbonate was added to the residue while cooling with ice, followed by washing with ethyl acetate. The aqueous phase was acidified with 1N HCl, and then extracted with ethyl acetate. The extract was washed with a saturated saline solution, dried over anhydrous magnesium sulfate and evaporated the solvent under reduced pressure. The residue thus obtained was recrystallized from a mixture of ethyl acetate and n-hexane, whereby 268 mg of a colorless needle crystal of the title compound was obtained (yield: 66%).

$^1$H NMR (CDCl$_3$: CD$_3$OD=9:1) δ: 1.28 (3H, t), 2.74 (3H, s), 2.75 (3H, s), 4.37 (2H, q), 5.34 (2H, s), 6.87 (1H, s), 7.23–7.41 (6H, m), 7.45–7.50 (1H, m), 7.85–7.88 (1H, m);

SIMS (m/z): 405 (M+1)+.

Preparation Example 1 Tablets

| Compound of Example 1 | 2.5 g |
|---|---|
| Lactose | 12 g |
| 6% HPC lactose | 8 g |
| Potato starch | 2 g |
| Magnesium stearate | 0.2 g |
| Total | 25 g |

All ingredients are blended together and compressed into 1000 tablets.

Preparation Example 2 Capsules

| | |
|---|---|
| Compound of Example 1 | 2.5 g |
| Lactose | 18 g |
| Potato starch | 4 g |
| Magnesium stearate | 0.5 g |
| Total | 25 g |

All ingredients are blended together and filled into hard capsules to prepare 1000 capsules.

Preparation Example 3 Formulation for Injection

| | |
|---|---|
| Compound of Example 2 | 0.5 g |
| Glucose | 7 g |
| Distilled water for injection | q.s. |

The compound in Example 2 and glucose are dissolved in distilled water for injection so that the total volume is 1000 ml. The solution is filtered with a glass filter and the 1 ml portions are distributed into 1000 ampoules.

Pharmacological Test (1) The angiotensin II antagonistic and antihypertensive activities of the compounds represented by formula (I) were examined by the following in vitro and in vivo test.

The angiotensin II antagonistic activities in vitro were compared on the basis of the intensities ($pA_2$ value) of antagonizing the contraction response to angiotensin II at the isolated thoracic aorta of rabbit. The in vivo activities were examined by comparing the inhibitory effects on the hypertensive action by an exogenous angiotensin II in a non-anesthetized rat and the hypotensive effects of a renal hypertensive rat or a spontaneously hypertensive rat.

1-1. In vitro angiotensin II antagonism

A strip of thoracic aorta of a male rabbit (2.5–3.0 kg) was prepared by the usual method and suspended in an organ bath containing well oxygenated Krebs-Henseleit solution at 37° C. The $pA_2$ value was calculated according to the method described by H. O. Schild (British Journal of Pharmacology and Chemotherapeutics, 2, 189–206, 1947). A strip treated with 3–5 doses of a subject compound in an amount of $10^{-6}M$–$10^{-10}M$ and a strip treated with no drug were employed for obtaining a dose-response curve by angiotensin II. Log (dose ratio—1) was calculated from the shift of the dose-response curve of the subject compound, and $pA_2$ value was obtained from the Schild plottings.

The results are shown in Table 5.

TABLE 5

| Example No. of subject compound | $pA_2$ | Example No. of subject compound | $pA_2$ |
|---|---|---|---|
| 1 | 8.28 | 46 | 9.21 |
| 3 | 8.24 | 53 | 8.52 |
| 11 | 8.20 | 55 | 7.91 |
| 12 | 8.76 | 57 | 8.21 |
| 16 | 9.04 | 67 | 9.89 |
| 21 | 8.17 | 68 | 8.23 |
| 44 | 9.00 | 81 | 8.01 |
| 45 | 8.17 | 83 | 7.55 |

1-2. Inhibition on the hypertensive action by an exogenous angiotensin II

Anesthetized Spraque-Dawley (SD) male rats were cannulated into a femoral artery and a femoral vein and used for the experiment at the time when it has elapsed at least 24 hours after the operation. The hypertensive action caused by angiotensin II (0.1 μg/kg) which has been administered through the vein catheter was measured under conscious and unrestrained condition before and after administration of the compound. The artery catheter was connected to a pressure transducer to measure a mean blood pressure, and the subject compounds were orally administered in the form of a homogeneous suspension in a 0.5% aqueous carboxymethyl cellulose solution.

As a result, significant inhibitory effects on the hypertensive action by angiotensin II were observed upon dose of 3 mg/kg of the compounds of Examples 21, 44, 53, 57, 68 and 81.

As for the compounds of Examples 1, 3, 11, 12, 16, 45, 46 and 83, significant inhibitory effects were also recognized in a dose of 1 mg/kg or less. The intensities of the inhibitory effects within 6 hours after administration of the compound were examined on the basis of the dose of the compound required for inhibiting the hypertensive action by angiotensin II to the extent of 50% ($ED_{50}$ values). The results are summarized in Table 6.

TABLE 6

| Example No. of subject compound | $ED_{50}$ (mg/kg) |
|---|---|
| 1 | 0.60 |
| 3 | 1.35 |
| 11 | 0.54 |
| 12 | 0.56 |
| 45 | 0.52 |
| 83 | 1.21 |

1-3. Hypotensive effect in renal hypertensive rats (RHR)

Renal hypertensive rats, a model of high-renin hypertension, were prepared according to the method of J. L. Cangiano et al. (Journal of Pharmacology and Experimental Therapeutics, 208, 310–313, 1979). That is, the experiment was conducted with Spraque-Dawley (SD) male rats (250–300 g), which were ligated the left renal artery with a thread under the anesthetic condition, so that the systolic blood pressure was increased more than 150 mmHg on 1 week after the operation. The subject compounds were orally administered in the form of a homogeneous suspension in a 0.5% aqueous carboxymethylcellulose solution, and a mean blood pressure was measured in the same manner as in the paragraph 1-2. Heart rate was counted with a cardiotachmeter triggered by the arterial pulse.

As a result, the compounds of Examples 11 and 45 depressed blood pressure to an extent of 20–26% at a dose of 3 mg/kg and thus .showed a significant long-lasting hypotensive effect.

1-4. Hypotensive effect in spontaneously hypertensive rats (SHR)

The subject compounds were administered orally in the same manner as in the paragraph 1-3 to male spontaneously hypertensive rats (28 weeks old, Charles-River Co.), which were measured mean blood pressure and heart rate.

As a result, the compounds of Examples 11 and 45 depressed blood pressure to an extent of approximately 20% at a dose of 10 mg/kg and thus showed a significant hypotensive effect.

(2) Antianxiety effect

The subject compounds were examined on their antianxiety effect with the light and dark box according to the method described by B. Costall et al. (Pharmacology Biochemistry and Behavior, 32, 777–785, 1989) and with the elevated plus maze by S. Pell et al. (Journal of Neuroscience Methods, 14, 149–167, 1985).

2-1. Light and dark box

The subject compounds were administered orally to ddY male mice (4–5 weeks old) at a dose of 0.1–1000 μg/kg. After 1 hour they were placed in the light chamber of the light and dark box, and after 10 seconds the door at the boundary between the light chamber and the dark chamber was opened. The behavior of the animals in the light and dark box under a sound-proof condition for four minutes was observed and examined by comparing the measurements of latency to the dark chamber, shuttling between the light and dark chambers and duration in the light chamber with those in the group to which only a solvent was administered. The subject compounds were orally administered in the form of a homogeneous suspension or solution in a 0.5% aqueous carboxymethyl cellulose solution.

As a result, in the group of the compound of Example 11 at a dose of 0.1 μg/kg, it was recognized that the latency to the dark chamber was increased and the duration in the light chamber was increased.

2-2. Elevated plus maze

To Fisher 344 male rats (5–6 weeks old), the subject compounds were orally administered at a dose of 1–100 μg/kg in the form of a homogeneous suspension or solution in a 0.5% aqueous carboxymethyl cellulose solution. Among the four arms of the elevated plus maze (a device in which four arms are intersected crosswise and connected together at a height of 50 cm from the floor), the two arms with side walls are referred to as closed arms and the two arms without side walls are referred to as open arms. After 1 hour from the administration of the compound, the animal was placed in the closed arm and the behavior was observed for 5 minutes. As the indices of the behavior, the latency until stepped out from the arm first placed to the other arm and the durations in the respective arms were measured, and the other behaviors were recorded. Diazepam was used as a control agent, and the drug administered group and the solvent administered group (group to which a 0.5% aqueous carboxymethyl cellulose solution was administered) were compared for the behaviors.

As a result, upon administering 3 mg/kg of diazepam as a typical antianxiety, the latency was significantly decreased and the transitions and the duration out of the closed arm was increased. In the same manner, the significant increase of transitions and the increasing tendency of the duration were recognized upon administering 1 μg/kg of the compound of Example 45.

(3) Cognitive enhancing effect

In order to examine the influence of the compounds on the learning and memory facilitating, an amnesia model with use of electric shock in a step through type passive avoidance box (PA-M5 model; OBARA IKASANGYOSHA) in accordance with the method described by C. Giurgea et al. (Progressive of Neuropsychopharmacology, 1, 235–247 (1977)) was used.

The subject compounds were orally administered at a dose of 1 ng/kg –1 mg/kg in the form of a homogeneous suspension in a 0.5% aqueous carboxymethylcellulose solution to ddY strain male mice (4–5 weeks) 1 hour before acquisition-trial and 1 hour before retrievaltrial. The animal was first placed in the light chamber, and the door at the boundary between the light and dark chamber was opened after 30 seconds. At the same time as the animal stepped into the dark chamber, electric footshock (40 V) was delivered to the floor of the dark chamber so that the animal acquired avoidance response (acquisition-trial). Next, the animal run back to the light chamber was taken out, and electric shock (40 mA, 0.5 s) was applied to the animal through the ear clip to cause amnesia. Retrieval-trial was conducted again after 24 hours. That is, the animal was placed again in the light chamber, the door was opened after 30 seconds, and the latency of the animal into the dark -chamber was measured for up to 600 seconds, so that the time was compared with that of the solvent administered group in which amnesia had been caused by electric shock.

As a result, the compound of Example 11 exhibited a significant prolongation of the latency into the dark chamber, that is, the improving effect at a dose of 10 μg/kg in the passive avoidance response of the electric shock induced amnesia mice.

(4) Toxicity test

Several compounds of the present invention represented by the general formula (I) were administered orally by compulsion to ddY male mice of 5 weeks old (average weight, ca. 20 g).

The results are summarized in Table 7.

TABLE 7

| Example No. of subject compound | $LD_{50}$ (mg/kg) |
|---|---|
| 1 | >1000 |
| 3 | >1000 |
| 11 | >1000 |
| 12 | >1000 |
| 45 | >1000 |
| 83 | >1000 |

In any compounds, no special symptoms were exhibited at a dose of 1000 mg/kg. Also, when the compound in Example 45 was administered orally to SD female rats (6 weeks old) at a dose of 100 mg/kg once daily for 2 weeks, no symptom of toxicity was observed.

What is claimed is:

1. A compound represented by the following formula:

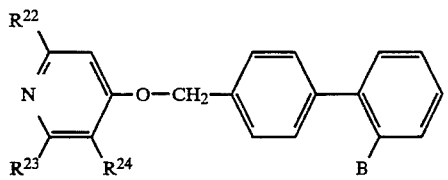

or a pharmaceutically acceptable salt thereof, wherein
$R^{22}$ and $R^{23}$ each independently represents methyl or ethyl;
$R^{24}$ represents a $C_{1-8}$ alkoxy which may be optionally substituted by halogen, $C_{3-7}$ cycloalkyl, or carbamoyl which may be optionally substituted by lower alkyl; lower alkenyloxy; $C_{3-7}$ cycloalkyloxy; or benzyloxy in which one or more hydrogen atoms on the phenyl group may be optionally substituted by halogen, lower alkyl, lower haloalkyl or lower alkoxy;
B represents a group $COOR^{18}$ wherein $R^{18}$ is hydrogen, lower alkyl or a group $-CH_2OCOC(CH_3)_3$; or tetrazolyl.

2. A compound as claimed in claim 1, wherein $R^{24}$ represents a $C_{1-8}$ alkoxy which may be optionally substituted by halogen, $C_{3-7}$ cycloalkyl, or carbamoyl which may be optionally substituted by lower alkyl; or benzyloxy in which one or more hydrogen atoms on the phenyl group may be optionally substituted by halogen, lower alkyl, lower haloalkyl or lower alkoxy.

3. A compound as claimed in claim 1, wherein $R^{24}$ represents a $C_{1-8}$ alkoxy or benzyloxy group.

4. A compound as claimed in claim 1, wherein $R^{24}$ represents a lower alkenyloxy or $C_{3-7}$ cycloalkyloxy group.

5. A compound as claimed in claim 1, which is selected from the group consisting of
2-ethyl-3-methoxy-6-methyl4-[2'-(tetrazol-5-yl)biphenyl-4yl]methoxypyridine,
3-methoxy-2,6-dimethyl-4-[2'-(tetrazol-5-yl)biphenyl-4yl]methoxypyridine,
3-ethoxy-2,6-dimethyl-4-[2'-(tetrazol-5-yl)biphenyl-4yl]methoxypyridine,
2,6-dimethyl-3-iso-propoxy-4-[2'(tetrazol-5-yl)biphenyl-4yl]methoxypyridine,
3-allyloxy-2,6-dimethyl-4-[2'-(tetrazol-5-yl)biphenyl-4yl]methoxypyridine,
3-benzyloxy-2,6-dimethyl-4-[2'-(tetrazol-5-yl)biphenyl-4yl]methoxypyridine, and pharmaceutically acceptable salts thereof.

6. 2-ethyl-3-methoxy-6-methyl-4-[2'-(tetrazol-5-yl)biphenyl-4-yl]methoxypyridine.

7. 3-methoxy-2,6-dimethyl-4-[2'-(tetrazol-5-yl)biphenyl-4-yl]methoxypyridine.

8. 3-ethoxy-2,6-dimethyl-4-[2'-(tetrazol-5-yl)biphenyl-4-yl]methoxypyridine.

9. 2,6-dimethyl-3-iso-propoxy-4-[2'-(tetrazol-5-yl)biphenyl-4-yl]methoxypyridine.

10. A pharmaceutical composition for treating hypertension, comprising an effective amount of a compound as defined in any one of claims 1 to 5 or a pharmaceutically acceptable salt thereof, together with one or a mixture of pharmaceutically acceptable carriers.

11. A method of treating hypertension, which comprises administering to a mammal an effective amount of a compound as defined in any one of claims 1 to 5 or a pharmaceutically acceptable salt thereof.

* * * * *